(12) United States Patent
Farokhzad et al.

(10) Patent No.: US 9,649,391 B2
(45) Date of Patent: May 16, 2017

(54) PARTICLES WITH MULTIPLE FUNCTIONALIZED SURFACE DOMAINS

(71) Applicants: Massachusetts Institute of Technology, Cambridge, MA (US); The Brigham and Women's Hospital, Inc., Boston, MA (US)

(72) Inventors: Omid C. Farokhzad, Chestnut Hill, MA (US); Carolina Salvador-Morales, Brookline, MA (US); Weiwei Gao, Cambridge, MA (US); Liangfang Zhang, San Diego, CA (US); Juliana M. Chan, Cambridge, MA (US); Robert S. Langer, Newton, MA (US)

(73) Assignees: Massachusetts Institute of Technology, Cambridge, MA (US); The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 15/097,676

(22) Filed: Apr. 13, 2016

(65) Prior Publication Data
US 2016/0228574 A1  Aug. 11, 2016

Related U.S. Application Data

(62) Division of application No. 13/122,654, filed as application No. PCT/US2009/059746 on Oct. 6, 2009, now Pat. No. 9,333,163.

(60) Provisional application No. 61/103,034, filed on Oct. 6, 2008.

(51) Int. Cl.
| | |
|---|---|
| A61K 9/50 | (2006.01) |
| A61K 47/48 | (2006.01) |
| A61K 8/14 | (2006.01) |
| A61K 8/86 | (2006.01) |
| A61K 49/00 | (2006.01) |
| A61Q 19/00 | (2006.01) |
| B82Y 5/00 | (2011.01) |
| A61K 31/7088 | (2006.01) |
| A61K 39/39 | (2006.01) |
| C12N 15/115 | (2010.01) |
| A61K 39/00 | (2006.01) |

(52) U.S. Cl.
CPC .......... *A61K 47/48915* (2013.01); *A61K 8/14* (2013.01); *A61K 8/86* (2013.01); *A61K 31/7088* (2013.01); *A61K 39/0005* (2013.01); *A61K 39/39* (2013.01); *A61K 47/48815* (2013.01); *A61K 47/48861* (2013.01); *A61K 47/48884* (2013.01); *A61K 49/0065* (2013.01); *A61K 49/0067* (2013.01); *A61K 49/0093* (2013.01); *A61Q 19/00* (2013.01); *B82Y 5/00* (2013.01); *C12N 15/115* (2013.01); *A61K 2039/55516* (2013.01); *A61K 2039/55555* (2013.01); *A61K 2039/6093* (2013.01); *C12N 2310/16* (2013.01); *C12N 2310/351* (2013.01); *C12N 2320/32* (2013.01)

(58) Field of Classification Search
CPC .. A61K 49/0002; A61K 9/143; A61K 9/5115; A61K 9/5153
USPC .............. 424/9.1, 9.3, 489–490, 497
See application file for complete search history.

(56) References Cited

U.S. PATENT DOCUMENTS

| | | |
|---|---|---|
| 5,118,528 A | 6/1992 | Fessi et al. |
| 5,741,138 A | 4/1998 | Rice et al. |
| 6,063,365 A | 5/2000 | Shefer et al. |
| 6,132,702 A | 10/2000 | Witt et al. |
| 6,426,513 B1 | 7/2002 | Bawendi et al. |
| 6,491,902 B2 | 12/2002 | Shefer et al. |
| 6,589,562 B1 | 7/2003 | Shefer et al. |
| 6,685,921 B2 | 2/2004 | Lawlor |
| 6,696,425 B2 | 2/2004 | Yerxa et al. |
| 6,825,161 B2 | 11/2004 | Shefer et al. |
| 7,375,234 B2 | 5/2008 | Sharpless et al. |
| 7,390,461 B2 | 6/2008 | Grier et al. |
| 2004/0058455 A1 | 3/2004 | Grier et al. |
| 2004/0131688 A1 | 7/2004 | Dov et al. |
| 2009/0105172 A1 | 4/2009 | Diener et al. |

FOREIGN PATENT DOCUMENTS

| | | |
|---|---|---|
| WO | 99/59811 | 11/1999 |
| WO | 00/17656 | 3/2000 |
| WO | 2007/150030 | 12/2007 |
| WO | 2008/124632 | 10/2008 |
| WO | 2009/051837 | 4/2009 |

OTHER PUBLICATIONS

Carreno et al., "The ability of Sephadex to activate human complement is suppressed in specifically subsitituted functional Sephadex derivatives," Mol. Immunol., 2:165-171 (1988).
Carreno et al., "Regulation of the human alternative complement pathway: formation of a ternary complex between factor H, surface bound C3b and chemical groups on nonactivating surfaces," Eur. J. Immunol., 19:2145-50 (1989).
Chumakova et al., "Composition of PLGA and PEI/DNA nanoparticles improves ultrasound-mediated gene delivery in solid tumors in vivo," Cancer Lett., 2:215-225.
Crepon et al., "Molecular weight dependency of the acquired anticomplementary and anticoagulant activities of specifically substituted dextrans," Biomaterials, 8:248-253 (1987).
De Smedt et al., "Cationic polymer based gene delivery systems," Pharm. Res., 2:113-126 (2000).

(Continued)

*Primary Examiner* — Micah-Paul Young
(74) *Attorney, Agent, or Firm* — Pabst Patent Group LLP

(57) ABSTRACT

This disclosure relates to particles (e.g., nanoparticles and microparticles) that display multiple functionalized surface domains in a controlled mosaic pattern. The disclosure also provides simple methods to create various particles that have multiple functionalized surface domains while allowing the use of a wide variety of diverse core structures. The multiple functionalized domains provide controllable particle binding and orientation, and controlled and sustained drug release profiles.

3 Claims, 13 Drawing Sheets

(56) References Cited

OTHER PUBLICATIONS

Hattori et al., "Low-molecular-weight polythelenimine enhanced gene transfer by cationic cholesterol-based nanopartical vector," Biol. Phar. Bull., 9:1773-78 (2007).

Javier et al., "Aptamer-targeted gold nanoparticles as molecular-specific contrast agents for reflectance imaging," Bioconjug. Chem., 6:1309-12 (2008).

Latil et al., "VEGF overexpression in clinically localized prostate tumors and neuropilin-1 overexpression in metastatic forms," Int. J. Cancer, 2:167-171 (2000).

Law and Reid, *Complement*, $2^{nd}$ ed., IRL Press, 43-45 (1995).

Luck et al., "Analysis of plasma protein adsorption on polymeric nanoparticles with different surface characteristics," J. Biomed. Mater. Res., 39:478-485 (1998).

Mauzac et al., "Anticomplementary activity of dextran derivatives," Biomaterials, 6:61-63 (1985).

Montdargent et al., "Interactions of functionalized polystyrene derivatives with the complement system in human serum," J. Biomater. Sci. Polym. Ed., 1:25-35 (1991).

Montdargent et al., "Regulation by sulphonate groups of complement activation induced by hydroxymethyl groups on polystyrene surfaces," Biomaterials, 3:203-208 (1993).

Pasqualini et al., "Searching for a molecular address in the brain," Mol. Psychiatry, 1:421-422 (1996).

Prabba et al., "Critical determinants in PLGA/PLA nanoparticle-mediated gene expression," Pharm. Res., 2:354-364 (2004).

Rajotte et al., "Molecular heterogeneity of the vascular endothelium revealed by in vivo phage display," J. Clin. Invest., 2:430-437 (1998).

Roh et al., "Biphasic Janus particles with nanoscale anisotropy," Nat. Materials, 4:759-763 (2005).

Salvador-Morales et al., "Complement activation and protein adsorption by carbon nanotubes," Mol. Immunol., 43:193-201 (2006).

Salvador-Morales et al., "Effects of covalent functionalization on the biocompatibility characteristics of multi-walled carbon nanotubes," J. Nanosci. Nanotechnol., 5:2347-56 (2008).

Salvador-Morales et al., "Immunocompatibility properties of lipid-polymer hybrid nanoparticles with heterogeneous surface functional groups," Biomaterials, 30:2231-40 (2009).

Vittaz et al., "Effect of PEO surface density on long-circulating PLA-PEO nanoparticles which are very low complement activators," Biomaterials, 16:1575-81 (1976).

Zhang et al., "Self-assembled lipid-polymer hybrid nanoparticles: a robust drug delivery platform," ACS Nano, 2:1696-1702 (2008).

Authorized Officer Lyu Eun Kyoung, International Search Report and Written Opinion in PCT/US2009/059746 mailed on May 3, 2010, 13 pages.

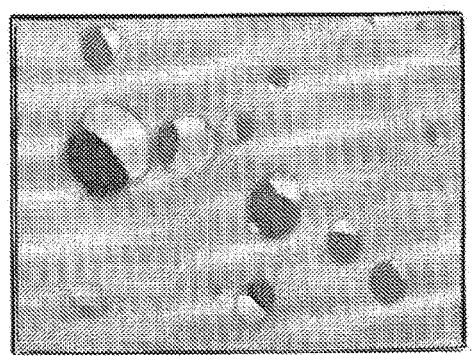 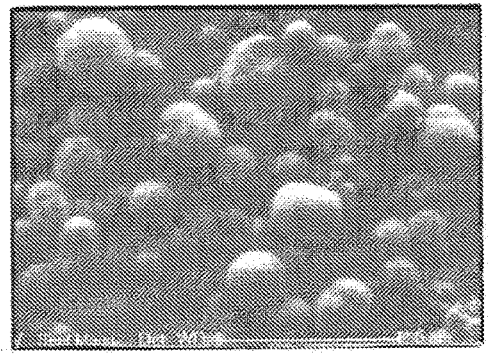
FIG. 16A    FIG. 16B
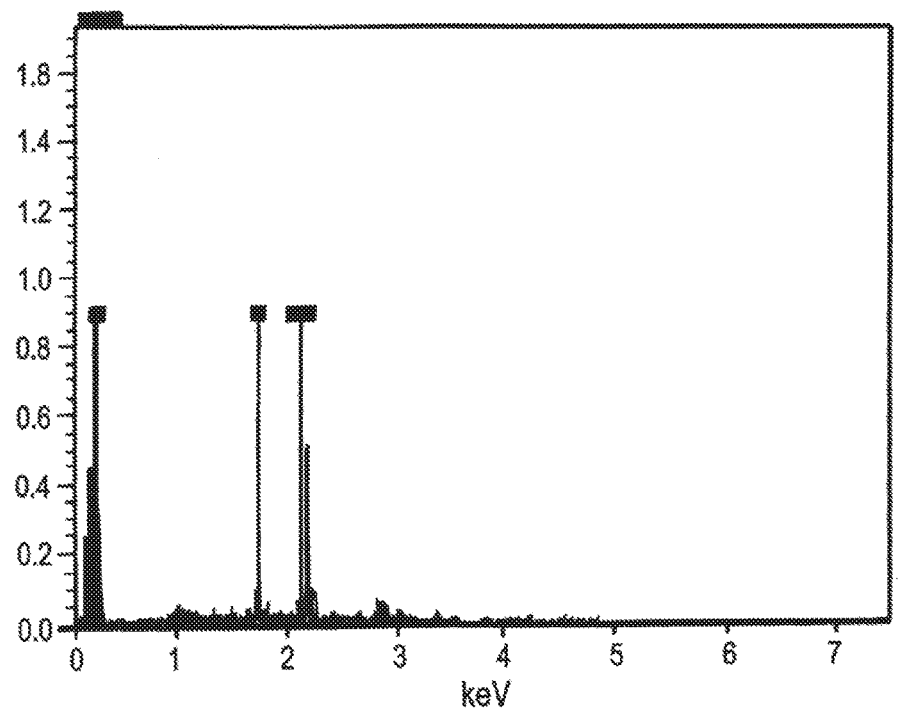
FIG. 16C

PARTICLES WITH MULTIPLE FUNCTIONALIZED SURFACE DOMAINS

CROSS-REFERENCE TO RELATED APPLICATIONS

This application is a divisional of application Ser. No. 13/122,654, which is a 371 of International Application No. PCT/US2009/059746, filed Oct. 6, 2009, which claims benefit of and priority to U.S. Provisional Application Ser. No. 61/103,034, filed on Oct. 6, 2008, which are hereby incorporated herein by reference in their entirety.

STATEMENT AS TO FEDERALLY SPONSORED RESEARCH

This invention was made with government support under Grant Nos. CA11939 and EB003647 awarded by the National Institutes of Health. The government has certain rights in the invention.

TECHNICAL FIELD

The invention relates to methods for the use and production of particles, such as nanoparticles or microparticles, with multiple functionalized surface domains.

BACKGROUND

Surface chemistry modifications of hard and soft submicron particles (micron and submicron) play a fundamental role in nanotechnology. Patterning techniques have been used to position tethers at specific locations on the particle surface, but a strategy for natural region selectivity on particles has not yet been reported. Pharmaceutical, nutraceutical, diagnostic, and cosmetic active ingredients/agents, for example, are optimally delivered and maintained near one or more target regions in an organism to expose the target tissue or cells to the desired active ingredients for a predetermined time and concentration. This so-called "drug targeting" modifies the pharmacokinetics and biodistribution of active ingredients to provide the potential for increased efficacy, while minimizing intrinsic toxicity.

SUMMARY

The invention is based, at least in part, on the discovery that you can prepare particles (e.g., nanoparticles and microparticles) that display multiple functionalized surface domains in a controlled mosaic pattern using simple and reproducible techniques. Such a mosaic segregation of functional groups on nanoparticles is demonstrated herein with different mixtures of functional groups, such as amine/methoxyl and amine/malemeide. Thus, the invention provides simple methods to create various particles that have multiple functionalized surface domains while allowing the use of a wide variety of diverse core structures. The multiple functionalized domains provide controllable particle binding and orientation, and controlled and sustained drug release profiles.

In one aspect, the invention features particles, e.g., micro- or nanoparticles, having multiple functionalized surface domains. The particles include a core structure having a surface; a plurality of first linkers, e.g., heterofunctional linkers, each including a first end that binds to the surface of the core structure, and a second end that includes a first functional group; and a plurality of second linkers, e.g., heterofunctional linkers, each including a first end that binds to the surface of the core structure, and a second end that includes a second functional group, different than the first; wherein the linkers are bound to the surface of the core structure via their respective first ends (and can extend outwards from the core surface), and wherein the first and second functional groups form an external mosaic of surface domains, each domain including a majority of one type of functional group. The new particles can include pluralities of three, four, or more of the linkers. In some embodiments, the first and second linkers can be the same except for the different functional groups. In certain embodiments, the particles can include three or more different linkers.

In the new particles, the mosaic can include two surface domains, a first domain including a majority of the first functional groups, and a second domain including a majority of the second functional groups. In other embodiments, the mosaic can include multiple surface domains each including a majority of first functional groups and multiple surface domains each including a majority of second functional groups. In these particles, the core structure can be or include an organic particle, an inorganic particle, or a particle comprising both organic and inorganic materials. For example, the core structure can be or include comprises a polymeric particle, a lipid-based particle, a metal particle, a quantum dot particle, a metal oxide particle, or a core-shell particle.

In various embodiments, the linkers can be or include a lipid, a surfactant, a polymer, a hydrocarbon chain, or an amphiphilic polymer. For example, the linkers can be or include polyethylene glycol or polyalkylene glycol. In certain embodiments, the first ends of the linkers include a lipid bound to polyethylene glycol (PEG) and the second ends comprise functional groups bound to the PEG.

The first and second (or more) functional groups can include an amine group, a maleimide group, a hydroxyl group, a carboxyl group, a pyridylthiol group, or an azide group. The first end of the first and second (or more) linkers can bind to the core structure surface by a covalent bond or a non-covalent bond. In certain examples, the first functional group can include a metal moiety and the core structure surface can include a metal chelator group, whereby the first functional group binds to the core structure surface by chelation.

In various embodiments, the core structure surfaces can include a plurality of hydrophilic or hydrophobic groups. In different embodiments, the core structure surface can include a quantum dot crystalline surface, a metal oxide surface, or a polymeric shell.

In certain embodiments, the particles described herein can include one or more targeting moieties, e.g., two or more distinct targeting moieties each bound to distinct surface domains. The targeting moiety or moieties can be or include a nucleic acid, nucleic acid ligand, polypeptide, protein ligand, small molecule, growth factor, hormone, cytokine, interleukin, antibody, antibody fragment, integrin, fibronectin receptor, carbohydrate, p-glycoprotein receptor, peptide, peptidomimetic, hydrocarbon, small modular immunopharmaceutical, or a cell binding sequence. For example, the protein ligands can be or include an affibody, nanobody, adnectin, domain antibody, or an avimer, or any combination thereof. For example, the targeting moiety can be a peptide comprising fewer than 8 amino acids, or the targeting moiety can bind to a basement membrane, or to the Prostate Specific Membrane Antigen (PSMA). In other embodiments, the targeting moiety or agent specifically binds to an antigen presenting cell.

In another aspect, the invention features the particles as described herein, further including an active agent. The active agent can be a biomolecule, bioactive agent, small molecule, drug, protein, peptide, vaccine, adjuvant, or polynucleotide, e.g., siRNA, microRNA, mRNA, or hnRNA. In various embodiments, the active agent is a vascular endothelial growth factor (VEGF), fibroblast growth factors monocyte chemoattractant protein 1 (MCP-1), transforming growth factor alpha (TGF-alpha), transforming growth factor beta (TGF-beta), DEL-1, insulin like growth factors (IGF), placental growth factor (PLGF), hepatocyte growth factor (HGF), prostaglandin E1 (PG-E1), prostaglandin E2 (PG-E2), tumor necrosis factor alpha (TBF-alpha), granulocyte stimulating growth factor (G-CSF), granulocyte macrophage colony-stimulating growth factor (GM-CSF), angiogenin, follistatin, and proliferin, PR39, PR11, nicotine, hydroxy-methylglutaryl coenzyme A (HMG CoA) reductase inhibitors, statins, niacin, bile acid resins, fibrates, antioxidants, extracellular matrix synthesis promoters, inhibitors of plaque inflammation and extracellular degradation, siRNA, or estradiol.

In another aspect, the invention features methods of making particles having multiple functionalized surface domains. The methods include obtaining a core structure having a surface; obtaining a plurality of first linkers, each having a first end that binds to the surface of the core structure, and a second end that has a first functional group; obtaining a plurality of second linkers, each having a first end that binds to the surface of the core structure, and a second end that includes a second functional group, different than the first; and binding the first ends of the linkers to the surface of the core structure via their respective first ends, wherein the first and second functional groups form an external mosaic of surface domains, each domain including one type of functional group.

In another aspect, the invention features other methods of preparing a polymeric nanoparticle having multiple functionalized surface domains. These methods include dissolving a polymer in a volatile, water-miscible organic solvent to form a first solution; dissolving a plurality of first and second amphiphilic components bound to linkers in an aqueous solvent to form a second solution, wherein the amphiphilic components each include a hydrophobic end and a hydrophilic end, the first linkers each include a first functional group, and the second linkers each includes a second functional group; and combining the first and second solutions such that a polymeric nanoparticle is formed having a polymer core surrounded by the amphiphilic components, wherein the linkers extend from the amphiphilic components and the first and second functional groups form an external mosaic of surface domains, each domain including one type of functional group.

In these methods, the first and second linkers can be the same except for the different functional groups, and the methods can further include obtaining a plurality of third (or fourth or more) linkers, different from the first and second linkers, and binding first ends of the third linkers to the surface of the core structure. In these methods, in certain embodiments, the final particles can have mosaic patterns that include two surface domains, a first domain including a majority of the first functional groups, and a second domain including a majority of the second functional groups. In other embodiments, the mosaic pattern can have multiple surface domains each including a majority of first functional groups and multiple surface domains each including a majority of second functional groups.

In various embodiments, the core structures can include an organic particle, an inorganic particle, or a particle including both organic and inorganic materials. For example, the particles can have a core structure that is or includes a metal particle, a quantum dot particle, a metal oxide particle, or a core-shell particle. For example, the core structure can be or include a polymeric particle or a lipid-based particle, and the linkers can include a lipid, a surfactant, a polymer, a hydrocarbon chain, or an amphiphilic polymer. For example, the linkers can include polyethylene glycol or polyalkylene glycol, e.g., the first ends of the linkers can include a lipid bound to polyethelene glycol (PEG) and the second ends can include functional groups bound to the PEG. In these methods, the first or second functional groups can include an amine group, a maleimide group, a hydroxyl group, a carboxyl group, a pyridylthiol group, or an azide group.

In certain embodiments, the polymers used in the new methods can be or include a sodium polystyrene sulfonate (PSS), polyethylene oxide (PEO), polyoxyethylene glycol, polyethylene glycol (PEG), polyethylene imine (PEI), polylactic acid, polycaprolactone, polyglycolic acid, poly(lactide-co-glycolide polymer (PLGA), cellulose ether polymer, polyvinylpyrrolidone, vinyl acetate, polyvinylpyrrolidone-vinyl acetate copolymer, polyvinyl alcohol (PVA), acrylate, polyacrylic acid (PAA), vinyl acetate, crotonic acid copolymers, polyacrylamide, polyethylene phosphonate, polybutene phosphonate, polystyrene, polyvinylphosphonate, polyalkylene, carboxy vinyl polymer, sodium alginate, carrageenan, xanthan gum, gum acacia, Arabic gum, guar gum, pullulan, agar, chitin, chitosan, pectin, karaya gum, locust bean gum, maltodextrin, amylose, corn starch, potato starch, rice starch, tapioca starch, pea starch, sweet potato starch, barley starch, wheat starch, hydroxypropylated high amylose starch, dextrin, levan, elsinan, gluten, collagen, whey protein isolate, casein, milk protein, soy protein, keratin, or a gelatin, or a copolymer, derivative, or mixture thereof.

In other embodiments, the polymer can be or include a polyethylene, polycarbonate, polyanhydride, polyhydroxyacid, polypropylfumerate, polycaprolactone, polyamide, polyacetal, polyether, polyester, poly(orthoester), polycyanoacrylate, polyvinyl alcohol, polyurethane, polyphosphazene, polyacrylate, polymethacrylate, polycyanoacrylate, polyurea, polystyrene, or a polyamine, or a copolymer, derivative, or mixture thereof.

In another aspect, the invention features methods methods of delivering an active agent to a biological target within a subject, the method including obtaining a pharmaceutical composition comprising a plurality of particles as described herein and a targeting agent bound to the particle, wherein the targeting agent binds specifically to the biological target; and administering to the subject the pharmaceutical composition in an amount effective to deliver the active agent in the particles to the biological target.

In these methods the particle can include first and second distinct targeting agents each binding preferentially to a different a specific cell type or molecule, and wherein the active agent includes a therapeutic agent. For example, the first targeting agent can bind, e.g., specifically bind, to a T cell and the second targeting agent can bind, e.g., specifically bind, to a cancer cell, and the therapeutic agent can activate the T cell to kill the cancer cell. In another example, the first targeting agent can bind, e.g., specifically bind, to an antigen presenting cell and the second targeting agent can bind, e.g., specifically bind, to a B cell, and the therapeutic agent can include an adjuvant.

In another aspect, the invention features methods of imaging a region of a subject, the method including obtaining a pharmaceutical composition comprising a plurality of particles as described herein and a targeting agent bound to the particle, wherein the active agent is an imaging agent and wherein the targeting agent binds specifically to a biological target in the region of the subject; administering to the subject the pharmaceutical composition in an amount effective to deliver the imaging agent in the particles to the region in the subject; and detecting the imaging agent to form an image of the region.

The invention also includes methods of treating a disorder in a subject in need thereof, the methods including administering to the subject an effective amount of the particles described herein, wherein the active agent is selected to treat the disorder, such as cancer.

In another aspect, the invention also features methods of vaccinating a mammalian subject, the methods including obtaining a particle as described herein, wherein a first functional group is bound to a targeting moiety that binds to an antigen presenting cell, and a second functional group is bound to a specific antigen, and administering to the subject an effective amount of the particle. In some embodiments, the particle can include one or more functional groups or active agents that activate the complement system in the mammalian subject, and the methods can further include administering the particle to a subcapsular sinus of a lymph node to selectively present the particle to subcapsular sinus macrophages.

In other aspects, the invention also includes personal care, agricultural, and food products that include particles as described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

Figure 12A:
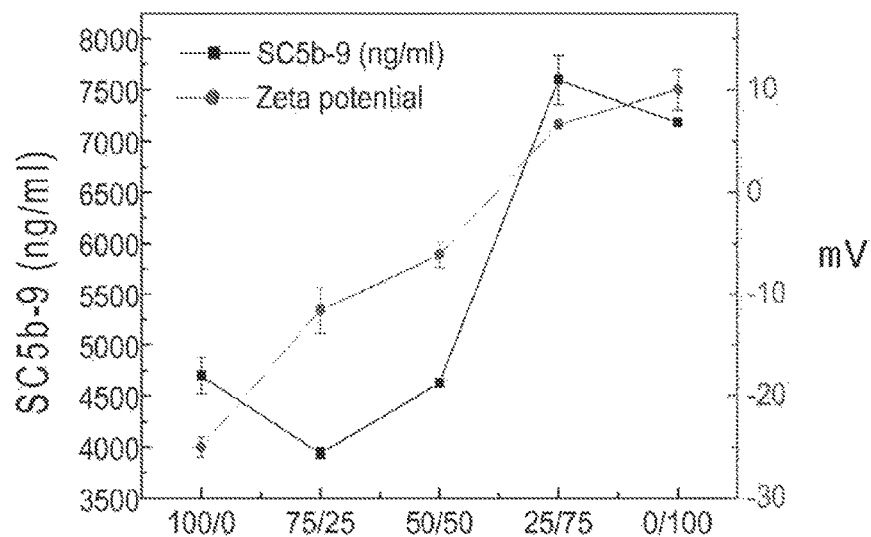
FIGS. 12A and 12B are a graph and a gel, respectively, that show the results of a human serum complement system activation assay and zeta potential using lipid-polymer hybrid nanoparticles as a function of carboxyl (NP—

COOH) and amine (NP—NH2)surface group compositions. Higher ratios of amine groups on the nanoparticle surface result in higher nanoparticle surface zeta potential (FIG. 12A) and higher complement activation. Apo C-III is the human serum protein that bound to NP—COOH/OCH$_3$ at all ratios: 100/0, 75/25, 50/50, 25/75, 0/100.

Figure 13A:
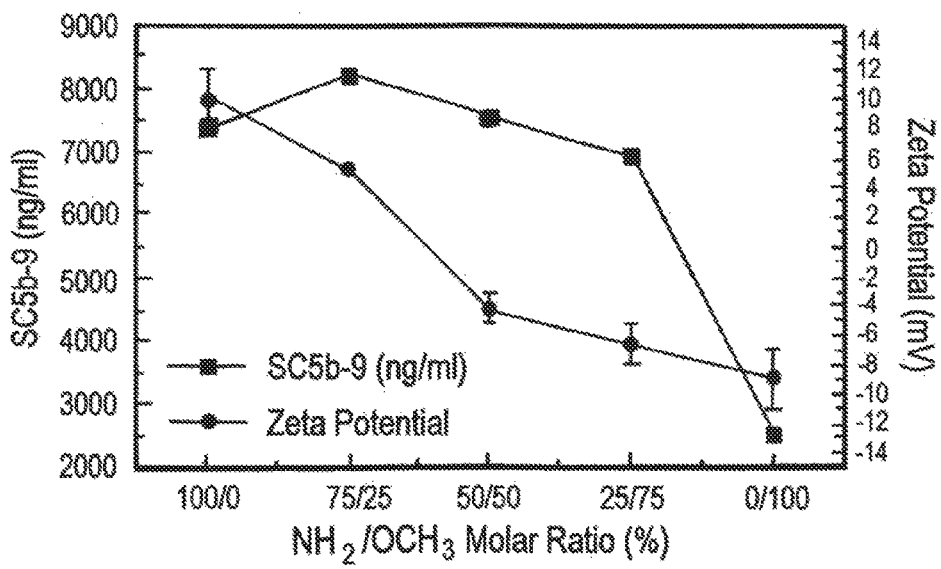
Figure 13B:
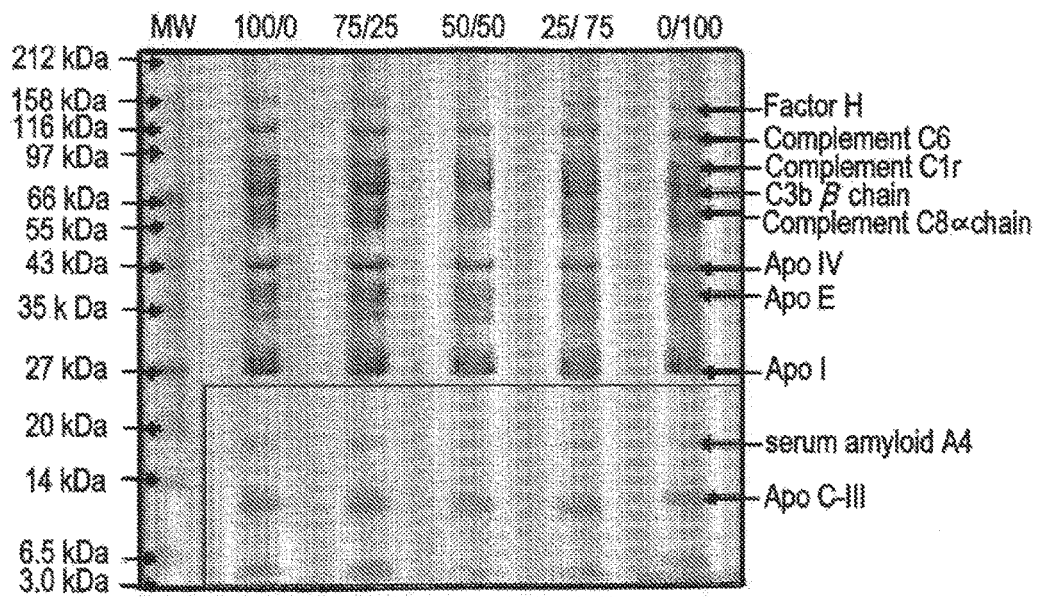

FIGS. 13A and 13B are a graph and a gel, respectively, that show the results of a human serum complement system activation assay and zeta potential using lipid-polymer hybrid nanoparticles as a function of amine (NP—NH$_2$) and methoxyl (NP—OCH$_3$) surface group compositions. Higher ratios of methoxyl groups on the nanoparticle surface led to smaller nanoparticle surface potential and lower complement activation. Serum amyloid A4 was bound to NP—NH$_2$/OCH$_3$ at all ratios except at 50/50% molar ratio, when the nanoparticle zeta potential is closest to neutral.

Figure 14:
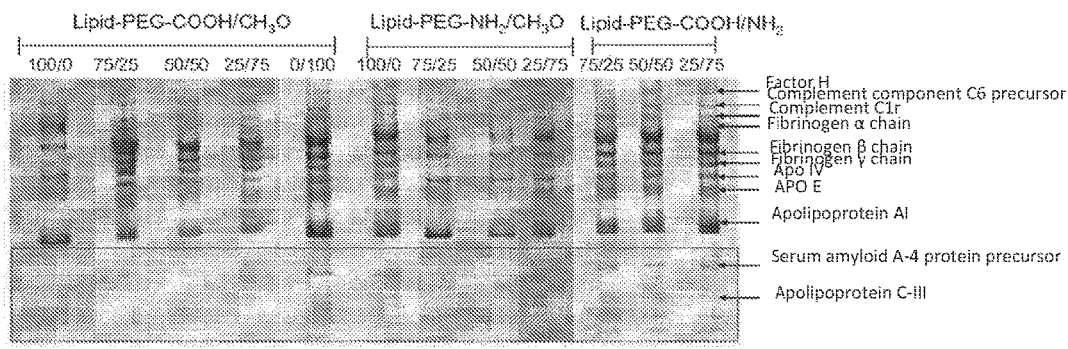

FIG. 14 is a gel that shows the results of human plasma proteins binding to the lipid-polymer hybrid nanoparticles as a function of surface functional group compositions.

Figure 15:
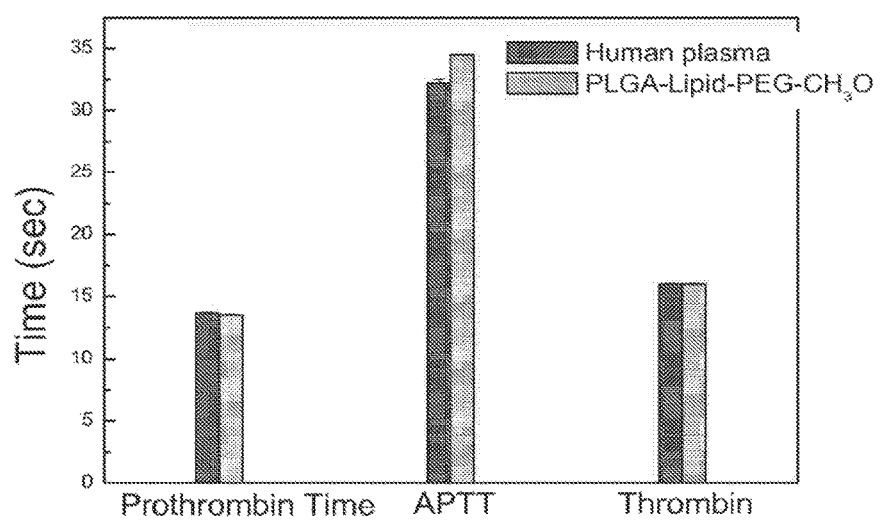

FIG. 15 is a bar graph that shows coagulation times (prothrombin time, activated partial thromboplastin time (APTT) and thrombin time) of human plasma in the absence and presence of lipid-polymer hybrid nanoparticles. Although fibrinogen can bind to receptors expressed by cells of the mononuclear phagocytic systems, results from lipid-polymer hybrid NP coagulation studies suggest that the binding of fibrinogen does not play a crucial role in those phenomena. Thus, coagulation assays suggest that these NPs do not affect the coagulation cascade.

FIGS. 16A, 16B, and 16C are images from TEM, Scanning Electron Microscope (SEM) and X-ray results of functionalized polymer microparticles. FIG. 16A is a TEM image of the polymeric microparticles with multiple functionalized surface domains. Microparticles were functionalized with 50% NH$_2$ and 50% MAL. Gold nanoparticles (black region) were used to trace the maleimide functional groups on the surface of the microparticles. FIG. 16B is a SEM image indicating again the polymeric microparticles with multiple functionalized surface domains. The maleimide functional groups were trace with gold nanoparticles (black). FIG. 16C is the energy dispersive X-ray indicating the presence of gold nanoparticles on half of the surface of the microparticles.

Figure 17A:
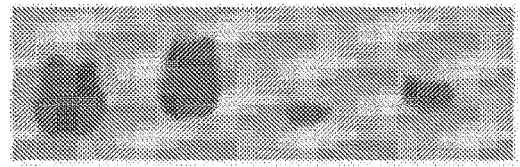

FIG. 17A is a Western blot showing results from unlabeled and labeled C3d bound to nanoparticles. Lane 1—Unlabeled C3d bound to nanoparticles; Lane 2—Labeled C3d bound to nanoparticles; Lane 3—unlabeled C3d (control); Lane 4—labeled C3d (control).

Figure 17B:
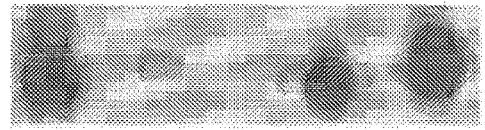

FIG. 17B is a Western blot showing results from unlabelled and labeled C3d bound to microparticles. Lane 1—Unlabeled C3d bound to nanoparticles; Lane 2—Labeled C3d bound to nanoparticles; Lane 3—unlabeled C3d (control); Lane 4—labeled C3d (control).

DETAILED DESCRIPTION

This disclosure describes new particles, e.g., nanoparticles and microparticles, which display multiple, different functionalized surface domains, which can be made in a reproducible and predictable manner, e.g., by using a single-step nanoprecipitation method. The new particles generally include a core structure (such as a organic or inorganic nanoparticle), and two or more different heterofunctional linkers, each having a first end that binds to the surface of the core structure, and a second end that includes a functional group. Each type of heterofunctional linker has a different type of functional group. The heterofunctional linkers are bound to the surface of the core structure via their respective first ends, and the different (e.g., two, three, four, or more) functional groups form an external mosaic of surface domains, each domain generally including a majority of one type of functional group.

The simplest type of these particles is the lipid-polymeric particle with multiple functionalized surface domains, which shows a mosaic segregation into two hemispheres. Other types of particles can have mosaic patterns of three, four, five, or more different types of functional groups. These polymeric particles present various unique features. First, the particles are typically symmetrical and display region-selectivity in the different domains that make up the external mosaic pattern. The different domains, e.g., two hemispheres, formed on the surface of the particles can trigger various preferential orientations, which, in turn, can be an asset for many widely varying applications, such as in drug delivery, vaccination, medical imaging, e.g., magnetic resonance imaging, and other medical applications, as well as personal care (such as cosmetics, hair care, and oral care products), nutrition (such as foods and beverages), and agricultural (e.g., fertilizers and pesticides) applications. Also the region-selectivity allows these new particles to be targeted to two or more different types of cells or organs within a subject in a single administration.

Second, the new particles, e.g., polymeric nanoparticles, functionalized with more than one type of functional group or moiety on their exterior can generate a cascade of functionalization, which allows further functionalization with a wide range of molecules (e.g., small molecules, biomolecules, organic and inorganic nanoparticles).

Third, the multiple surface domains, or compartments, are formed simply by mixing different functional groups in different percentages, e.g., using EDC/NHS, and maleimeide/SH reactions, and other methods described herein. Thus, the methods of producing these new particles are easy, cheap, practical, reproducible, and scalable.

In addition, the new multifunctional particles, e.g., polymeric micro- and nanoparticles, can be produced such that they are biodegradable, such that they include materials already approved by FDA, and such that they result in a submicron size (e.g., 10 nm-1000 nm or more, e.g., 25-250 nm, e.g., 15 to 50 nm, 10 nm-500 nm), or a micron-scale size. Nano-scale particles are generally considered to be up to 1000 nm at their largest cross-sectional dimension. Micron-scale particles are over 1.0 micron at their largest cross-sectional dimension (e.g., 1.0 micron up to 100 microns, or larger, e.g., 1.0 to 2.0 microns, 1.0 to 10.0 microns, 5 to 25 microns, and 25 to 50 microns), can also be made according to the methods described herein.

In some cases, the particle is a nanoparticle, i.e., the particle has a characteristic dimension of less than about 1 micrometer, where the characteristic dimension is the largest cross-sectional dimension of a particle. For example, the particle may have a characteristic dimension of less than about 500 nm, less than about 250 nm, less than about 150 nm, less than about 100 nm, less than about 50 nm, less than about 30 nm, less than about 10 nm, less than about 3 nm, or less than about 1 nm in some cases.

In some cases, a population of particles may be present. Various embodiments of the present invention are directed to such populations of particles. For instance, in some embodiments, the particles may each be substantially the same shape and/or size ("monodisperse"). For example, the particles may have a distribution of characteristic dimensions such that no more than about 5% or about 10% of the particles have a characteristic dimension greater than about 10% greater than the average characteristic dimension of the particles, and in some cases, such that no more than about 8%, about 5%, about 3%, about 1%, about 0.3%, about 0.1%, about 0.03%, or about 0.01% have a characteristic dimension greater than about 10% greater than the average characteristic dimension of the particles. In some cases, no more than about 5% of the particles have a characteristic dimension greater than about 5%, about 3%, about 1%, about 0.3%, about 0.1%, about 0.03%, or about 0.01% greater than the average characteristic dimension of the particles.

In some embodiments, the diameter of no more than 25% of the produced particles varies from the mean particle diameter by more than 150%, 100%, 75%, 50%, 25%, 20%, 10%, or 5% of the mean particle diameter. It is often desirable to produce a population of particles that is relatively uniform in terms of size, shape, and/or composition so that each particle has similar properties. For example, at least 80%, at least 90%, or at least 95% of the particles produced using the methods described herein can have a diameter or greatest dimension that falls within 5%, 10%, or 20% of the average diameter or greatest dimension. In some embodiments, a population of particles may be heterogeneous with respect to size, shape, and/or composition. See, e.g., PCT WO 2007/150030, which is incorporated herein by reference in its entirety.

This disclosure also describes methods of making these new particles, e.g., by spontaneous organization of heterogeneous surface functional groups (self-assembly process). Such methods can be carried out using crosslinking agents to attach molecules including quantum dots, ferritin, and polyester beads that have carboxyl or amine ends for binding sites, thus providing different types of functional group for the nanoparticles.

This particle design emerges by functionalizing the surface of a wide range of polymeric particles, including lipid-polymeric hybrid particles, PLGA, PLA, etc, with two or more different surface functional groups mixed in different percentages. For example, particles can be functionalized with combinations of 50% amine or carboxylic groups and with 50% of malemeide surface functional groups. As described in more detail below, such combinations enable the new particles to bind to various combinations of different biomolecules (antibodies, proteins, peptides, aptamers, etc.) as well as organic and inorganic molecules (fullerenes, carbon nanotubes, etc.) to each of the different functional domains in the external mosaic surface, and thus can be used in a wide variety of applications.

For example, one type of the new particles, lipid-polymer hybrid nanoparticles provide a unique and novel therapeutic design that is useful to treat different types of disorders in various subjects including people and animals, such as mammals, e.g., dogs, cats, cows, pigs, goats and horses, and birds and fish, as well as plants, e.g., agricultural and food crops. These nanoparticles combine characteristics of both liposomes and polymer particles and are able to carry poorly soluble drugs in high capacity. Their circulation half-life is longer than that of polymeric particles, and a bit shorter than that of liposomes. These sophisticated and elegant particles have multivalent targeting abilities and can be designed to provide a sustained and/or controlled drug release.

Particles with Multiple Functionalized Surface Domains

The present invention includes a new class of particles (e.g., nanoparticles or microparticles) that generally include a central core structure and multiple different functional groups on the external surface, arranged in a mosaic pattern of surface domains (e.g., clusters) of the different function groups, with each domain or cluster including a majority of the same type of functional group. The different functional groups provide different surface chemistries and surface physicochemical properties, and thus the new particles are capable of delivering active ingredients or bio-functional agents to two or more different targets within a specific environment, e.g., the body of a human or animal subject, the skin, other organs (e.g., eye, heart, liver, pancreas, lungs, and prostate) or hair of a subject, or the leaves or roots of a plant. The new particles can be loaded with a wide variety of active agents, e.g., therapeutic agents, for enhanced drug targeting and delivery, and/or enhanced efficacy of the active ingredient.

Figure 1:
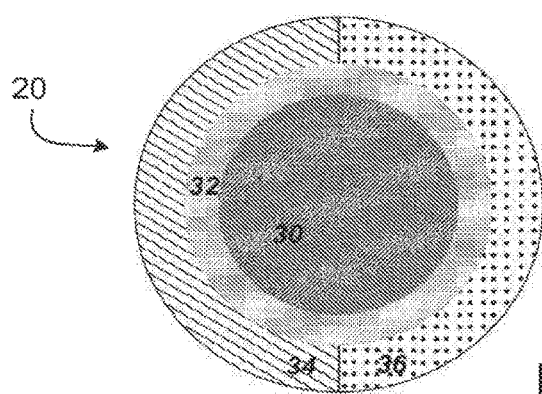
FIG. 1 is a schematic diagram of a polymeric particle, e.g., a microparticle or nanoparticle, with two separate functional surface domains.

In one general aspect, FIG. 1 shows a schematic representation of a particle have a plurality, here two, different and distinct functional groups arranged in an external mosaic pattern. Particle 20 includes a core structure 30 that has bound to it a plurality of two different types of heterofunctional linkers that form an interfacial region 32 outside the particle core 30. There are two different types of surface functional groups or moieties 34 and 36, which are arranged in an external mosaic pattern of spatially discrete domains or compartments. In this general representation, particle 20 is functionalized with a first domain of a first type of functional group 34 and also with a second, different domain of a second type of functional group 36. Of course, in other embodiments, there may be several domains that contain the first type of function group, interspersed between the second type of functional groups (like multiple islands or clusters of one functional group in a "sea" of the second functional group). Alternatively, the two or more different functional groups can form domains or clusters that are equally and/or symmetrically distributed across the surface of the external mosaic pattern, e.g., as in the surface of a soccer ball. In general, only a small portion of the particles, e.g., nanoparticles are found in which the mosaic pattern cannot readily be observed, possibly due to the surface functional groups mixing in a homogeneous fashion. In these embodiments, there may not be separate clusters of the functional groups (or the clusters are very small), but rather the two or more functional groups are homogenously distributed.

The multiple surface domains are all exposed to the external environment, thus providing exposure to each of the respective distinct functional groups to the external environment. This design provides enhanced environmental interface and optimum diffusion or material transfer, resulting in increased bioavailability for each of the functional groups.

Figure 2A:
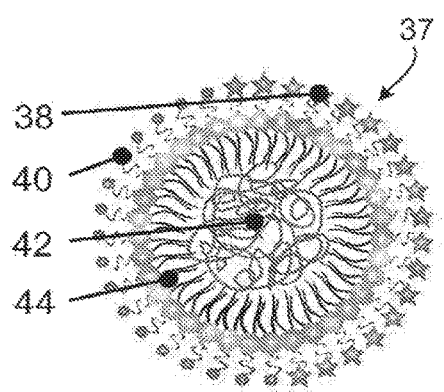
FIG. 2A is a schematic diagram of a polymeric particle with two different types of functional groups forming an external mosaic of two surface domains, each domain having one type of functional group.

FIGS. 2A-2F illustrate in schematic form various alternative embodiments of the new particles, each having multiple different functional groups on the external surface, arranged in a mosaic pattern of surface domains (e.g., clusters) of the different function groups, with each domain or cluster including a majority of the same type of functional group. For example, FIG. 2A shows a lipid-polymer particle that can be prepared by using various ratios of different polymers. Particle 37 is functionalized with a first surface functional group 38 and a second, different surface functional group 40 and includes a central core polymer 42, which is surrounded by two different types of heterofunctional linkers 44, that each includes a lipid (e.g., lecithin) and a polyethylene glycol (PEG) molecule, with the functional groups attached to the PEG.

For example, using 50:50 molar ratio of the linkers lecithin-PEG-maleimide (LPM) and lecithin-PEG-NH$_2$ (LPN) results in an equal distribution of these two different functional groups (maleimide and amine). For example, LPM and LPN can be dissolved in 4% ethanol in water. The central core polymer 42, e.g., PLGA (or PLA), can be dissolved in a variety of volatile organic solvent, including acetonitrille, acetone, ethyl acetate, and dichloromethane (DCM), followed by precipitation into LPN and LPM solvent at elevated temperature (~70° C.). As the organic solvent evaporates, nanoparticles with 50% $NH_2$ and 50% maleimide surface functional groups arranged in a simple hemispherical mosaic pattern will form.

In a similar fashion, nano- or microparticles can be prepared using the emulsion method. PLGA or PLA can be dissolved in a volatile organic solvent such as acetonitrille, acetone, ethyl acetate, and DCM. The polymer solvent can be emulsified using a homogenizer (either once or twice) with an aqueous solution that contains 50% DSPE-PEG-$NH_2$ and 50% DSPE-PEG-MAL (molar ratio) and 4% (weight percent) ethanol. After the organic solvent evaporates, microparticles with 50% $NH_2$ and 50% maleimide surface functional groups will form.

Figure 2B:
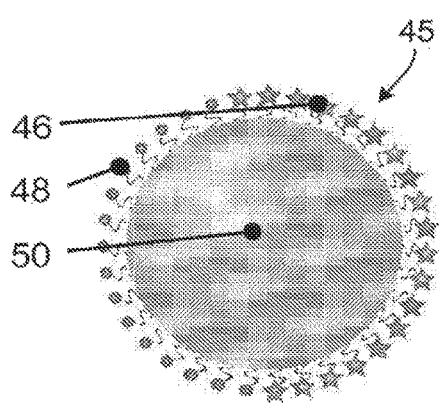
FIG. 2B is a schematic diagram of a metal particle with two different types of functional groups forming an external mosaic of two surface domains, each domain having one type of functional group.

FIG. 2B illustrates particles formed with a metallic core. Particle 45 includes a metallic core structure 50 that is stabilized by interacting with heterofunctional linkers that include the two different functional groups 46 and 48. These linkers can bind to the metallic core structure through mostly, but not limited to, covalent chemical interactions. As a specific example, gold particles can be stabilized using heterofunctional linkers that include PEG that has a thiol group at one end and a functional group at the other end. The thiol group forms a covalent bond with the surface of the gold. To make particles functionalized with multiple surface domains, two different PEG linkers are used, one that has a first function group and the other that has a second functional group. The gold particles and heterofunctional PEG linkers are incubated to form gold particles with multiple distinct surface functional groups arranged in an external mosaic pattern, e.g., two hemispheres or other patterns.

Figure 2C:
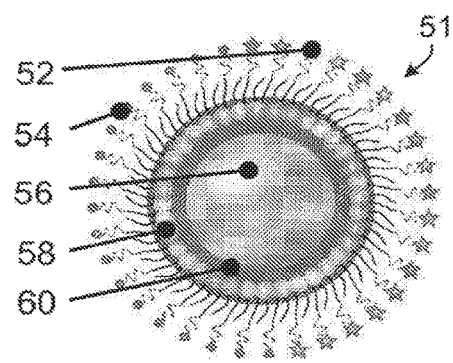
FIG. 2C is a schematic diagram of a reverse micelle particle with two different types of functional groups forming an external mosaic of two surface domains, each domain having one type of functional group.

FIG. 2C illustrates another variation of the new particles. Here, particle 51 is formed by separating aqueous droplets of small size (nm or micrometer) from a bulk organic solvent by a surfactant layer. Particles 51 are functionalized with a first surface functional group 52 and a second, different surface functional group 54. The particles consist of an aqueous droplet 56 in the core surrounded by reverse surface ligand 58 which is in a bulk organic solvent 60. To make these particles, heterofunctional linkers with distinct terminal functional groups (e.g., —$NH_2$, —COOH, or -maleimide) at one end are chosen. The particle size, stability, and composition depend on the conditions in formulation process, such as precipitation or emulsification, and on the temperature and material compositions.

In addition, a variety of aqueous soluble materials, such as active agents, e.g., drugs, can be encapsulated inside the water droplet within the core structure 56 of these particles. Active agents also include, but are not limited to, proteins, small hydrophilic molecules, nucleic acids, and metal or metal oxide colloidal particles.

Figure 2D:
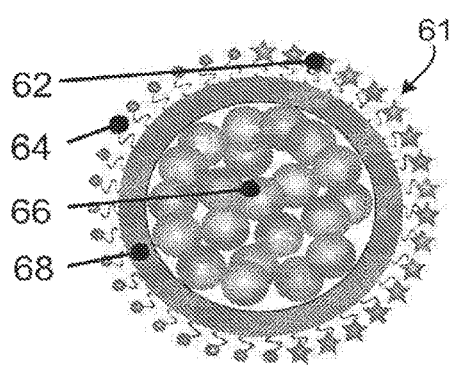
FIG. 2D is a schematic diagram of a quantum dot particle with two different types of functional groups forming an external mosaic of two surface domains, each domain having one type of functional group.

FIG. 2D shows another variation of the invention. Particle 61 is functionalized with a first surface functional group 62 and a second, different surface functional group 64, and comprises quantum dot crystals as the core structure 66. Quantum dots usually exist in the form of nano- or micrometer scale crystals. Amphiphilic polymers can be used to stabilize these crystals in the solution. The hydrophobic tails of amphiphilic polymers point towards the quantum dot crystals and the hydrophilic heads extend towards the aqueous solution, creating a quantum dot crystalline surface region 68. Stable nanoparticles form through a self-assembly process. By choosing amphiphilic polymers with different terminal functional groups (at the hydrophilic head), different quantum dot particles with multiple distinct surface functional groups arranged in an external mosaic pattern will form.

Figure 2E:
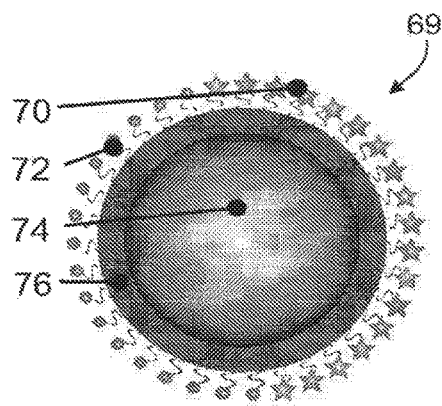
FIG. 2E is a schematic diagram of a metal oxide particle with two different types of functional groups forming an external mosaic of two surface domains, each domain having one type of functional group.

In another variation, as shown in FIG. 2E, the particles 69 include a metal oxide core structure 74 and are functionalized with a first surface functional group 70 and a second, different surface functional group 72. The metal oxide core 74 is surrounded by a metal oxide surface region 76. Examples of such metal oxide particles include thermally cross-linked superparamagnetic iron oxide nanoparticles (SPIONs), monocrystalline iron oxide nanoparticles (MION) and cross-linked iron oxide nanoparticles (CLIOs). The metal oxide core is stabilized by interaction with functional ligands through a variety of interactions such as hydrophobic-hydrophilic interactions, hydrogen bonding, and covalent bonding. To form particles with multiple surface functional domains, heterofunctional linkers are used, as with the other particles described herein. These linkers all have one common terminal functional group that can interact with metal oxide cores. However, they have different functional groups on the other end. Through the self-assembly process, metal oxide particles with different domains of surface functional groups can be formed.

Figure 2F:
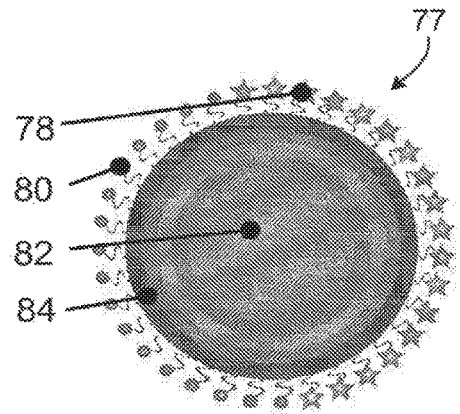
FIG. 2F is a schematic diagram of a core-shell particle with two different types of functional groups forming an external mosaic of two surface domains, each domain having one type of functional group.

FIG. 2F shows another variation, in which so-called "core-shell" particles 77 are functionalized with a first surface functional group 78 and a second, different surface functional group 80. Many particles can form the core 82 and shell structures 84. These particles can be made of metals, metal oxides, polymers, and hybrids or combinations of these materials. The heterofunctional linkers that stabilize these particles can be lipids or polymers, or combinations. The linkers interact with the core-shell particle through a variety of interactions such as hydrophobic-hydrophilic interactions, hydrogen bonding, and covalent bonding. These linkers all have one common terminal functional group that can interact with, e.g., bind to, the core-shell core structure 82. However, they have different functional groups on the other end. The self-assembly process can be used to form these core-shell particles with different surface domains of functional groups arranged in a mosaic pattern.

The new particles can have a variety of shapes or morphologies, and can comprise materials in a solid phase or a semi-solid phase, although liquid phases are contemplated in certain variations. The various shapes and morphologies, include, by way of non-limiting example, spheres, rectangles, polygons, disks, toroids, cones, pyramids, rods/cylinders, fibers, and the like. Nano-fibers generally have an elongated axial dimension that is substantially longer than the other dimensions of the nano-fiber.

In various embodiments, at least one component of the particle comprises at least one polymer. In certain aspects, the polymers can also be modified by chemical or physical methods, such as cross-linking, heat treatment, photochemical treatment, and/or changes in the chemical or physical environment. In certain aspects, the polymer modification occurs to different degrees, potentially resulting in different materials or materials responses, as appreciated by one of skill in the art. Such polymer modifications and/or treatments provide different release kinetics in certain aspects.

Suitable non-limiting polymers for use in the embodiments of the invention as described in FIG. 2A-2F include sodium polystyrene sulfonate (PSS), polyethers, such as a polyethylene oxide (PEO), polyoxyethylene glycol or polyethylene glycol (PEG), polyethylene imine (PEI), a biodegradable polymer such as a polylactic acid, polycaprolactone, polyglycolic acid, poly(lactide-co-glycolide polymer (PLGA), and copolymers, derivatives, and mixtures thereof. Other polymers are well known to those of skill in the art for use in pharmaceutical, diagnostics, oral care, and personal care compositions, such as polyvinylpyrrolidone. Specifically, at least one phase can be designed to have one or more of the following properties based upon material selection: hydrophobic, positively-charged (cationic), negatively-charged (anionic), polyethylene glycol (PEG)-ylated, covered with a zwitterion, hydrophobic, superhydrophobic (for example having with water contact angles in excess of 150°.), hydrophilic, superhydrophilic (for example, where the water contact angle is near or at 0°.), olephobic/lipophobic, olephilic/lipophilic, and/or nanostructured, among others. In other aspects, one or more polymers or materials used within the particle may be functionalized to subsequently undergo reaction with various moieties or substances after formation of the multiphasic nano-component, to provide desired surface properties or to contain various moieties presented on the phase surface, as recognized by those of skill in the art.

Water-soluble and/or hydrophilic polymers, which are cosmetically and pharmaceutically acceptable, include cellulose ether polymers, including those selected from the group consisting of hydroxyl alkyl cellulose, including hydroxypropyl methyl cellulose (HPMC), hydroxypropyl cellulose (HPC), hydroxyethyl cellulose (HEC), methyl cellulose (MC), carboxymethyl cellulose (CMC), and mixtures thereof. Other polymers among those useful herein include polyvinylpyrrolidone, vinyl acetate, polyvinylpyrrolidone-vinyl acetate copolymers, polyvinyl alcohol (PVA), acrylates and polyacrylic acid (PAA), including polyacrylate polymer, vinylcaprolactam/sodium acrylate polymers, methacrylates, poly(acryl amide-co-acrylic acid) (PAAm-co-AA), vinyl acetate and crotonic acid copolymers, polyacrylamide, polyethylene phosphonate, polybutene phosphonate, polystyrene, polyvinylphosphonates, polyalkylenes, and carboxy vinyl polymer. The multifunctional surface functional group embodiments described herein can include derivatives, copolymers, and further combinations of such polymers, as well.

Other polymers and water-soluble fillers useful herein include, without limitation, sodium alginate, carrageenan, xanthan gum, gum acacia, Arabic gum, guar gum, pullulan, agar, chitin, chitosan, pectin, karaya gum, locust bean gum, various polysaccharides; starches such as maltodextrin, amylose, corn starch, potato starch, rice starch, tapioca starch, pea starch, sweet potato starch, barley starch, wheat starch, modified starch (e.g., hydroxypropylated high amylose starch), dextrin, levan, elsinan and gluten; and proteins such as collagen, whey protein isolate, casein, milk protein, soy protein, keratin, and gelatin. Other useful polymers are described, for example, in PCT WO 2008/124632, which is incorporated herein by reference in its entirety.

Methods of Making Particles with Multiple Functionalized Surface Domains

There are two general ways of making the new particles, depending on the core structure. If the core structure is a pre-existing particle, then the methods involve binding of multiple different types of heterofunctional linkers, each with their specific type of functional group, to the surface of the core structure. If the core structure is self-assembled along with the linking of the heterofunctional linkers to the surface of the self-assemble core structure, then other methods, such as a single-step nanoprecipitation.

The single-step nanoprecipitation methods are described in U.S. Pat. No. 5,118,528, which is incorporated herein by reference. These methods can be used to synthesize nanoparticles by mixing a solution containing a substance into another solution (i.e., a non-solvent) in which the substance has poor solubility. For example, polymeric (e.g., PLGA-PEG) nanoparticles can be made in which polymer solutions in either water-immiscible or water-miscible solvents are added to an aqueous fluid (i.e. the non-solvent). Such nanoprecipitation methods are also described, for example, in PCT WO 2007/150030, which is incorporated herein by reference in its entirety.

In general, if the core structure already exists, the methods of making particles having multiple functionalized surface domains generally include (i) obtaining a core structure having a surface; (ii) obtaining a plurality of first heterofunctional linkers, each including a first end that binds to the surface of the core structure, and a second end that includes a first functional group; (iii) obtaining a plurality of second heterofunctional linkers, each having a first end that binds to the surface of the core structure, and a second end that includes a second functional group, different than the first; and (iv) binding the first ends of the heterofunctional linkers to the surface of the core structure via their respective first ends, wherein the first and second functional groups form an external mosaic of surface domains, each domain comprising one type of functional group.

Various methods are known to link or bind a heterofunctional linker to a core structure using covalent bonds (such as including σ-bonding, π-bonding, metal to non-metal bonding, agnostic interactions, disulfide bonds, and three-center two-electron bonds) and non-covalent bonds (such as hydrogen bonds, ionic bonds, Van der Waals forces, and hydrophobic interactions) to form the new particles. In one example, a bond, e.g., crosslinking, can be achieved by forming an amide bond between carboxyl (or malemide) and a primary amine by using 1-ethyl-3-[3-dimethylaminopropyl] carbodiimide hydrochloride/N-hydroxysuccinimide (EDC/NHS) or benzotriazole-1-yl-oxy-tris-pyrrolidino-phosphonium hexafluorophosphate/N-hydroxybenzotriazole (pyBOP/HOBt). The reaction can tolerate both aqueous and organic solvents (such as, but not limited to, dichloromethane, acetonitrile, chloroform, tetrahydrofuran, acetone, formamide, dimethylformamide, pyridines, dioxane, or dimethysulfoxide).

In another example, binding, e.g., crosslinking is formed between maleimide and sulfhydryl (thiol) groups in both aqueous and organic solvents. A reduction cleavable crosslinking can be achieved between sulfhydryl (thiol) group, through the pyridylthiol group, 3-nitro-2-pyridylthio (Npys) group, and Boc-S-tert-butylmercapto (StBu) group. The reaction can tolerate both aqueous and organic solvents (such as, but not limited to, dichloromethane, acetonitrile, chloroform, tetrahydrofuran, acetone, formamide, dimethylformamide, pyridines, dioxane, or dimethysulfoxide).

In another example, micro-scale particles may be produced where crosslinking is achieved by forming an amide bond between carboxyl (or malemide) and primary amine groups by using EDC/NHS or SPDP (N-Succinimidyl 3-[2-pyridyldithio]-propionate) in both aqueous and organic solvents (such as, but not limited to, dichloromethane, acetonitrile, chloroform, tetrahydrofuran, acetone, formamide, dimethylformamide, pyridines, dioxane, or dimethysulfoxide).

In another example, so-called "click chemistry" can be used to attach the functional surface groups to the core structures of the particles (see, e.g., the Sigma Aldrich catalog and U.S. Pat. No. 7,375,234, which are both incorporated herein by reference in their entireties). Of the reactions comprising the click chemistry field, one example is the Huisgen 1,3-dipolar cycloaddition of alkynes to azides to form 1,4-disubstituted-1,2,3-triazoles. The copper (I)-catalyzed reaction is mild and very efficient, requiring no protecting groups, and requiring no purification in many cases. The azide and alkyne functional groups are generally inert to biological molecules and aqueous environments. The triazole has similarities to the ubiquitous amide moiety found in nature, but unlike amides, is not susceptible to cleavage. Additionally, they are nearly impossible to oxidize or reduce.

In one aspect, this process is used to catalyze a click chemistry ligation reaction between a first reactant having a terminal alkyne moiety and second reactant having an azide moiety for forming a product having a triazole moiety. More particularly, the click chemistry ligation reaction is catalyzed by an addition of Cu(II) in the presence of a reducing agent for reducing said Cu(II) to Cu(I) (or by the addition of Cu(I)), in situ, in catalytic amounts. Useful reducing agents include ascorbate, metallic copper, quinone, hydroquinone, vitamin $K_1$, glutathione, cysteine, $FE^{2+}$, $Co^{2+}$, and an applied electric potential. Further reducing agents include metals selected from Al, Be, Co, Cr, Fe, Mg, Mn, Ni, and Zn.

The metallic copper contributes directly or indirectly to the catalysis of the click chemistry ligation reaction. In one embodiment, the solution is an aqueous solution. The first and second reactants can be present during the click chemistry ligation reaction in equimolar amounts. Also, the click chemistry ligation reaction can be performed in a solution in contact, at least in part, with a copper vessel. In other embodiments the reaction can be catalyzed by the addition of a catalytic amount of a metal salt having a metal ion selected from the group Au, Ag, Hg, Cd, Zr, Ru, Fe, Co, Pt, Pd, Ni, Rh, and W, e.g., in the presence of a reducing agent, as noted above, for reducing the metal ion to a catalytically active form.

If the central core structure is self-assembled, such as certain polymeric particles and lipid-containing particles, such as micelles and reversible micelles, then the methods generally include (i) dissolving a polymer in a volatile, water-miscible organic solvent to form a first solution; (ii) dissolving a plurality of first and second amphiphilic components bound to heterofunctional linkers in an aqueous solvent to form a second solution, wherein the amphiphilic components each have a hydrophobic end and a hydrophilic end, the first heterofunctional linkers each include a first functional group, and the second heterofunctional linkers each include a second functional group; and (iii) combining the first and second solutions such that a polymeric nanoparticle is formed having a polymer core surrounded by the amphiphilic components, wherein the heterofunctional linkers extend from the amphiphilic components and the first and second functional groups form an external mosaic of surface domains, each domain generally including a majority of one type of functional group.

Figure 3:
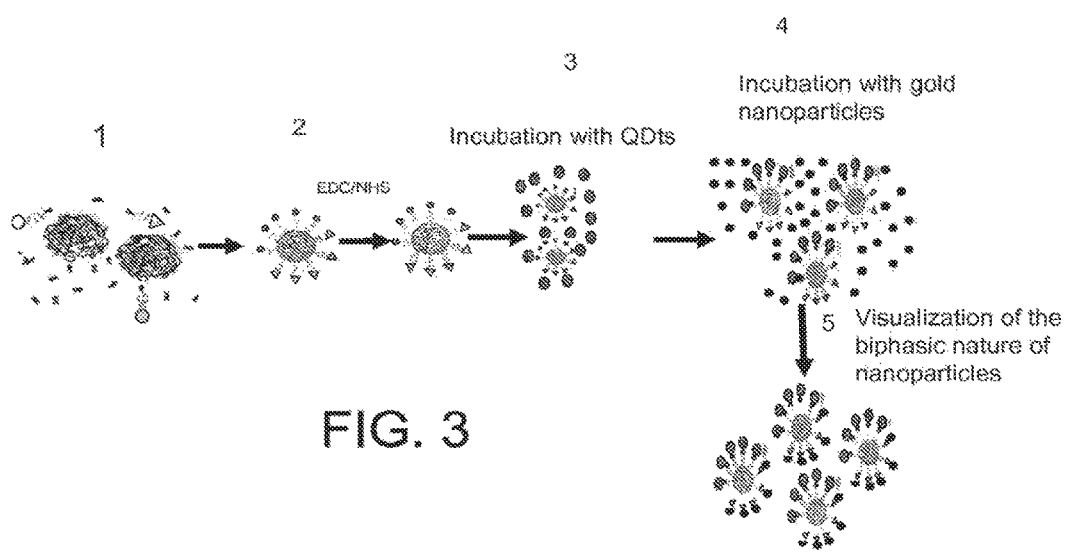
FIG. 3 is a schematic representation of a process of forming polymeric lipid-polymer nanoparticles with multifunctional surface domains.

In a more specific embodiment, FIG. 3 shows a representation of a process by which biodegradable lipid-polymer particles with multiple different surface domains can be made. To synthesize segregated hemispheres of a mosaic pattern, two different functional groups intercalated in 50% molar ratio in the polymer core of the hybrid nanoparticle can be used. For instance, PLGA-Lecithin-PEG-R nanoparticles, where R can be the functional group carboxyl, methoxyl, amine, or maleimide, can be synthesized by a modified nanoprecipitation method. Particles are incubated with EDC/NHS reaction, steps 1 and 2. The NHS-activated nanoparticles were reacted with carboxylated quantum dots in step 3. In turn, PLGA-Lecithin-PEG-$NH_2$-QDts nanoparticles were incubated with gold nanoparticles in step 4. Quantum dots and gold nanoparticles make visible the dual surface domains of these nanoparticles (step 5).

A general protocol as follows can be used to make particles with multiple function surface domains. To synthesize segregated external hemispheres of two different functional groups, two different functional groups intercalated in a molar ratio, e.g., 10:90, 20:80, 30:70, 40:60, 50:50, 60:40, 70:30, 80:20, or 90:10, can be linked to the polymer core of the hybrid nanoparticles using heterofunctional linkers. For example, lipid-polymer hybrid nanoparticles using PLGA-Lecithin-PEG-can be prepared by functionalizing half of the particles with a first functional group, e.g., $NH_2$, and the other half with methoxyl or maleimide functional groups. Of course, the ratios can be different. In addition, one can have three, four, or more different functional groups in various ratios, e.g., 20:60:20, 25:50:25, 33⅓:33⅓:33⅓, 30:40:30, 40:20:40, etc. The PLGA-Lecithin-PEG-$NH_2$ molecules are suspended in water and incubated with NHS and EDC for a time sufficient to yield NHS-activated particles, e.g., 20-40 minutes, e.g., 30 minutes.

Particles are then washed three times with MQ water followed by ultrafiltration. The NHS-activated particles are resuspended in PBS and reacted with carboxylated quantum dots for a time sufficient to bind the quantum dots, e.g., 30 to 120 minutes, e.g., 60 to 90 minutes, e.g., 60 minutes. The resulting PLGA-Lecithin-PEG-$NH_2$-QDts bioconjugate can be washed, e.g., three times, with MQ water. Any excess quantum dots are removed by pipetting out the supernatant after the third wash. Immediately PLGA-Lecithin-PEG-$NH_2$-QDts particles are resuspended in PBS and maintained at a near neutral pH, e.g., 7.4. Gold nanoparticles are added to the nanoparticles and incubated for a sufficient time to promote binding, e.g., 1 to 3 hours, e.g., 2 hours, followed by three washes.

Figure 4A:
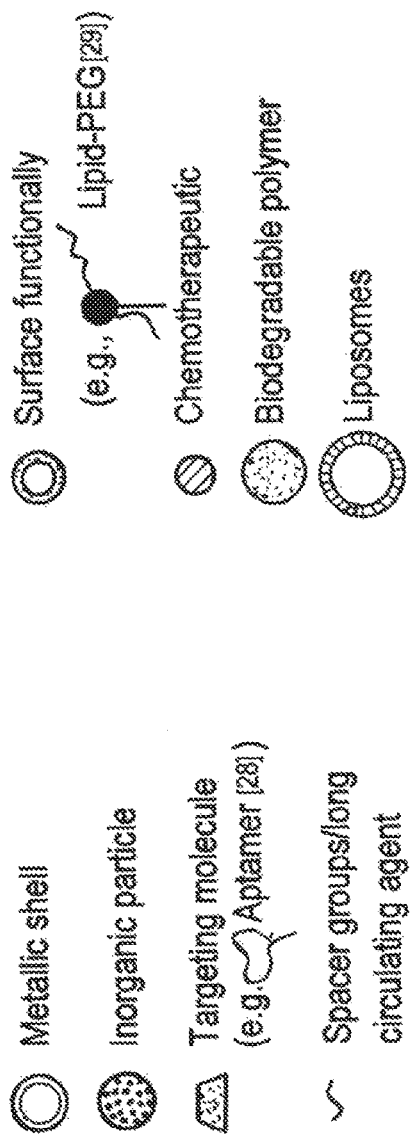
FIG. 4A is a schematic of a biodegradable polymeric nanocarrier capable of encapsulating hydrophobic or hydrophilic drugs in its matrix and releasing the drugs upon degradation.
Figure 4A:
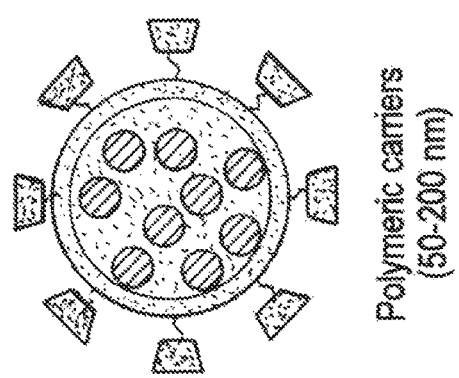
Figure 4B:
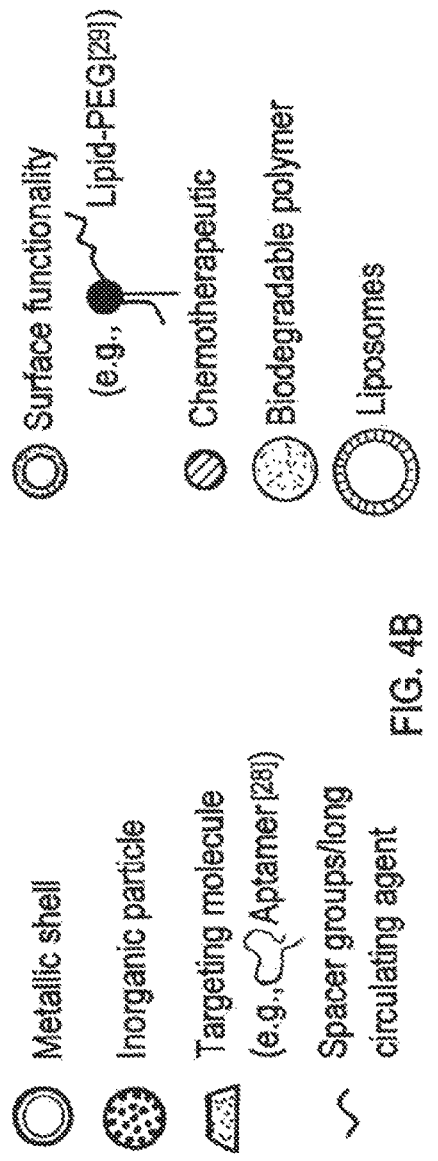
FIG. 4B is a schematic of a metal nano-shell particle that can work as a dual platform, for both imaging and therapy.
Figure 4B:
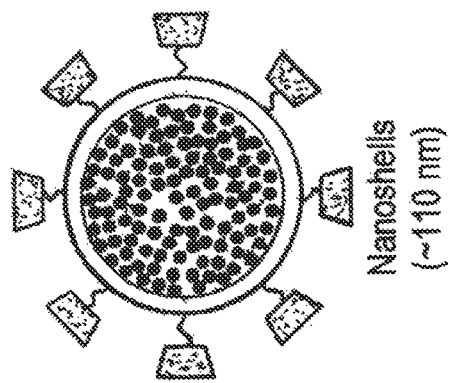
Figure 4C:
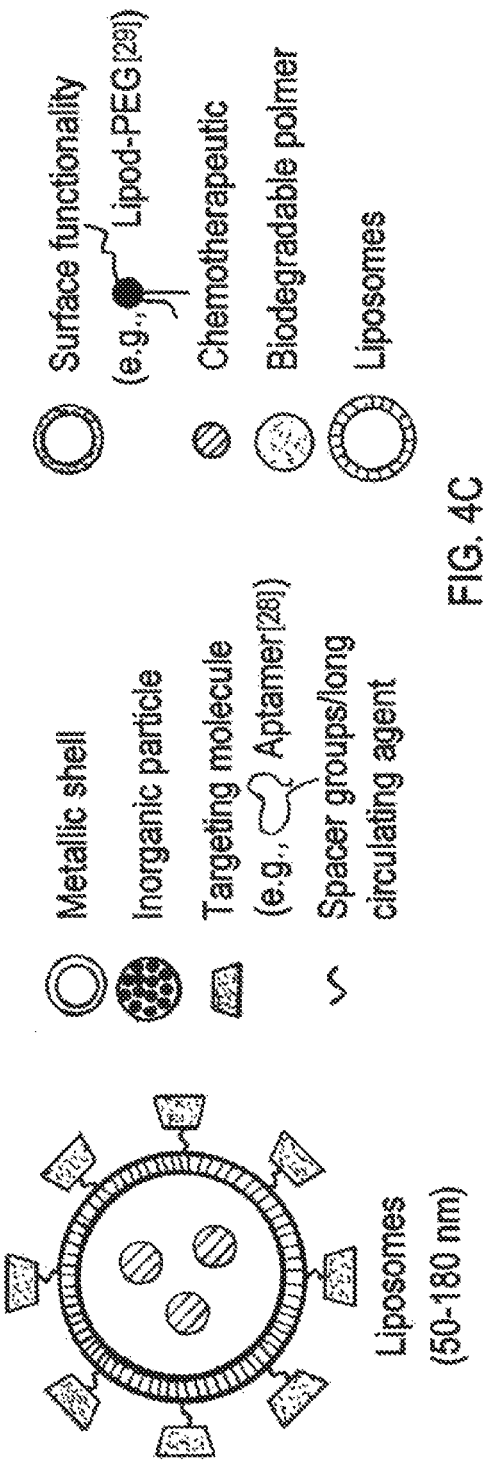
FIG. 4C is a schematic of a liposome as a nanoparticles-based carrier for delivering anticancer drugs.

Loading Active Agents into or onto Particles with Multiple Functionalized Surface Domains The delivery of active agents, such as therapeutic agents, is one of the most distinctive functions of the new particles described herein. FIGS. 4A, 4B, and 4C illustrate three different types of particles that can be used to carrier various active agents. In various aspects, the particles can be in the form of a polymeric carrier (FIG. 4A), a nano-shell (FIG. 4B), or in the form of a liposome (FIG. 4C), all of which can be loaded with a wide variety of active agents depending on the desired application.

An active agent is a compound or composition that diagnoses, prevents, or treats a physiological or psychological disorder or condition, or can provide a cosmetic or aesthetic benefit. In certain aspects, an active agent is targeted to a particular target, such as organs, tissues, medical implants or devices, hair, skin, mouth, eyes, circulatory system, and the like, as described in more detail below. For example, in various aspects, the new particles having one or more active ingredients can be used in various pharmaceutical and/or cosmetic compositions. A "pharmaceutically and/or cosmetically acceptable composition" refers to a material or combination of materials that are used with mammals or other organisms having acceptable toxicological properties for beneficial use with such an animal. Pharmaceutically and/or cosmetically acceptable compositions include drug and therapeutic compositions, oral care compositions, nutritional compositions, personal care compositions, cosmetic compositions, diagnostic compositions, and the like.

In certain aspects, the pharmaceutically and/or cosmetically acceptable compositions can include medical devices and implants, or surface films, or coatings for such devices. The particles can be used in a wide variety of different types of compositions having a bio-functional or bio-active material and are not limited to the variations described herein.

The following description of suitable active agents is exemplary and should not be considered limiting as to the scope of active agents that can be introduced into the new particles described herein. All suitable active agents known to those of skill in the art for various uses and types of compositions are contemplated. Suitable active agents for use in such pharmaceutically and/or cosmetically acceptable compositions are well known to those of skill in the art and include, by way of example, pharmaceutical active agents found in the Merck Index, An Encyclopedia of Chemicals, Drugs, and Biologicals, Thirteenth Edition (2001) by Merck Research Laboratories and the International Cosmetic Ingredient Dictionary and Handbook, Tenth Ed., 2004 by Cosmetic Toiletry and Fragrance Association, each incorporated herein by reference.

Certain suitable active agents, or pharmaceutically active agents or drugs, include, but are not limited to, low-molecular weight molecules, quantum dots, natural and artificial macromolecules, such as proteins, sugars, peptides, DNA, RNA, and the like, polymers, dyes and colorants, inorganic ingredients including microparticles, nanoparticles, nanomaterials, and nanocrystals, fragrances, and mixtures thereof.

A variety of low molecular weight molecules can be employed, particularly those having a molecular weight of less than about 10,000, optionally less than about 1,000, and optionally less than about 500. Such molecules include therapeutic drugs, which by way of non-limiting example includes chemotherapeutic drugs, such as doxorubicin (molecular mass of about 543.5 g/mol); paclitaxel or Taxol™ (molecular mass of about 853.9 g/mol), cholesterol lowering drug, lovastatin (molecular mass of about 404.5 g/mol), NSAID analgesic ibuprofen (molecular mass of 206.3 g/mol). Quantum dots are optically active nanostructures, for example, cadmium tellurium (CdTe). Other active agents include macromolecules, which include a wide range of compounds, generally including polymers and biomolecules having relatively large molecular weights. Such macromolecules can be naturally occurring or synthesized. A variety of polymers well known to those of skill in the art can be employed if the polymers are smaller than the core structure in which they are distributed. Amino acids, peptides (amino acids linked via peptide bonds); polypeptides (linear chains of peptides); and proteins (primary, secondary, and tertiary folded polypeptides) are all contemplated as active agents. Exemplary active agent proteins include heat shock protein 70 (HSP70) for dendritic cells and folic acid for cancer cells. Exemplary toxins for use as active agents include saporin and Botulinum toxins. Exemplary sugars include silylic acid leukocytes and glucuronic acid, for example.

Useful active agents in the form of nanoparticles and nanocrystals generally having a particles size of less than about 50 nm, optionally less than about 20 nm, and in some aspects, less than 10 nm. Useful non-limiting active agents in the form of nanoparticles include magnesium oxide, and metal based nanoparticles, comprising gold, silver, and the like. Suitable active agent nanocrystals include magnetite ($Fe_3O_4$).

Suitable, non-limiting examples of active agents in the form of drugs include 5-Fluorouracil (5-FU): an anti-metabolite drug commonly used in cancer treatment. Typical dosing begins with intravenous treatment at 400 mg/m² (i.e., per square meter of calculated body surface area) over 15 minutes as a bolus, then an ambulatory pump delivers 2,400 mg/m² as a continuous infusion over 46 hours. Suitable chemotherapeutic drugs can be divided into the following classes: alkylating agents, antimetabolites, anthracyclines, plant alkaloids, topoisomerase inhibitors, monoclonal antibodies, and other anti-tumor agents. In addition to the chemotherapeutic drugs described above, namely doxorubicin, paclitaxel, other suitable chemotherapy drugs include tyrosine kinase inhibitor imatinib mesylate (Gleevec® or Glivec®), cisplatin, carboplatin, oxaliplatin, mechloethamine, cyclophosphamide, chlorambucil, azathioprine, mercaptopurine, pyrimidine, vincristine, vinblastine, vinorelbine, vindesine, podophyllotoxin (L01CB), etoposide, docetaxel, topoisomerase inhibitors (L01CB and L01XX) irinotecan, topotecan, amsacrine, etoposide, etoposide phosphate, teniposide, dactinomycin, and monoclonal antibodies, such as trastuzumab (Herceptin®), cetuximab, bevacizumab and rituximab (Rituxan®), among others.

Other examples of therapeutic moieties include, but are not limited to, antimicrobial agents, analgesics, antinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, parasympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable therapeutic moieties include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

In certain embodiments, the particles include lovastatin, a cholesterol lowering and heart disease active agent, which can be included within the nanoparticles described herein. In another aspect, a suitable active agent included in core of the particle is Phenytoin, an anticonvulsant agent (marketed as Dilantin®) in the USA and as Epanutin® in the UK by Pfizer, Inc). Antibiotics can be incorporated into the particle, such as vancomycin, which is frequently used to treat infections, including those due to methicillin resistant staph aureus (MRSA). The particle optionally includes cyclosporin, a lipophilic drug that is an immunosuppressant agent, widely used post-allogeneic organ transplant to reduce the activity of the patient's immune system and the risk of organ rejection (marketed by Novartis under the brand names Sandimmune®, the original formulation, and Neoral® for the newer microemulsion formulation). Particles comprising cyclosporine can be used in topical emulsions for treating keratoconjunctivitis sicca, as well. In this regard, particles with multifunctional surface domains incorporating such drugs can be designed to deliver equivalent dosages of the various drugs directly to the cancer cells, thus potentially minimizing the amount delivered generally to the patient and minimizing collateral damage to other tissues.

In certain specific aspects, the particles of the present disclosure include one or more of: non-steroidal anti-inflammatory agents (NSAIDs), analgesics, COX-I and II inhibitors, and the like. For example, indomethacin is a suitable NSAID suitable for incorporation into a multiphase nano-component of the disclosure.

Other active agents in the form of therapeutic agents are described in PCT WO 2008/124632, which is incorporated herein by reference in its entirety.

As described above, active agents can be suitable for use in a wide variety of applications and include proteins, peptides, sugars, lipids, steroids, DNA, RNA, low-molecular weight drugs. Such active agents can be suspended in a polymer solution or a polymer melt, which is then used to form the core structure of the new particles. In one embodiment, the particles can be loaded with an active agent or multiple active agents.

The core of the particles can also include secondary sustained and/or controlled release systems, such as nanoparticles with sizes equal or smaller than the core, liposomes, polysomes, or dendrimers. Each of the secondary release systems can be include multiple types of active agents, as well, permitting a staging of release of a plurality of active agents. The secondary release systems can be formed with the same materials described above in the context of the multiphasic nano-components, however, can be distributed throughout a phase (for example as a continuous and discontinuous phase mixture). Thus, the secondary release system provides an additional amount of control over the release kinetics of active ingredients based and provides an even greater range of complex design and delivery options.

In yet another set of embodiments the new particles described herein can include a chelating moiety, i.e., a moiety that can bind one or more ions, typically divalent (or higher) ions such as $Ca^{2+}$, $Mg^{2+}$, or $Fe^{2+}$. An example of such a moiety is ethylenediamine tetraacetic acid. In another set of embodiments the moiety can have multiple charged groups, e.g., under physiological conditions.

Active agents can also include materials and compositions useful in the personal care, cosmetics, food, and agricultural industries. Specific examples are recited below in the methods of use discussion.

Methods of Targeting Particles with Multiple Functionalized Surface Domains

Certain drug targeting techniques have suffered from challenges when such active ingredients are administered to target tissue or introduced into the circulatory system of a living organism, i.e., when used in vivo. For example, certain nano-scale particles have been observed to be rapidly cleared by the liver and the spleen. Further, in some examples, the active ingredients combined with nanoparticles may trigger or activate an immune system response in the organism. For example, it is believed that certain nanoparticles (for example, certain nanoparticles having an average diameter above 200 nm) activate the complement system of mammalian immune systems. Different sub-types of macrophages recognize and rapidly clear invading particulates, such as the foreign drug delivery vehicles, in various mammals. In addition, the pre-adsorption of blood-borne proteins often facilitates recognition by macrophages. Thus, drug targeting can be more effective if the carrier and delivery systems for such active ingredients are improved.

Generally, drug targeting can be classified into two classes, passive and active drug targeting. Passive drug targeting strategies take advantage of pathophysiological or anatomical properties of an organism, whereas active targeting strategies often involve selective affinity or binding of a construct that recognizes and specifically or preferentially binds to a particular target (e.g., a biological target, such as a specific cell, tissue, organ, receptor, antigen, or cell-surface marker). For example, a targeting agent or moiety, such as an antibody, a peptide, a ligand, or an aptamer, can be conjugated to a functional group on the new particles, which can also contain or be bound (via a different functional group in the external mosaic pattern) to an active agent or ingredient.

In contrast to known targeting moieties, such as liposomes and polysomes, the present disclosure provides particles, comprised of polymers or non-polymer materials, which display multiple functional groups in an external mosaic pattern. These particles can be symmetrical and display region-selectivity. The symmetry of the two hemispheres, or multiple surface domains, can trigger a preferential orientation that can be an asset for many applications.

In accordance with certain aspects of the present disclosure, the multifunctional particles are suitable for use in a wide variety of biofunctional or bioactive applications. Specific delivery of the new particles to achieve these biofunctional and bioactive results can be achieved by attaching the right targeting agents or moieties to at least one of the multiple different functional groups. A "biofunctional" or "bioactive" substance refers to a chemical substance, such as a small molecule, macromolecule, metal ion, or the like, that causes an observable change in the structure, function, optical function, or composition of a cell when a cell is exposed to such a substance. Examples of observable changes include increased or decreased expression of one or more mRNAs, increased or decreased expression of one or more proteins, phosphorylation of a protein or other cell component, inhibition or activation of an enzyme, inhibition or activation of binding between members of a binding pair, an increased or decreased rate of synthesis of a metabolite, increased or decreased cell proliferation, changes in optical properties, and the like. In certain aspects, the particles of the disclosure deliver active ingredients to a target, in some embodiments, to tissue or an organ of an organism. In other aspects, the particles provide binding to certain target regions in an organism to modify optical or physical properties to improve diagnostic and imaging procedures.

Figure 5:
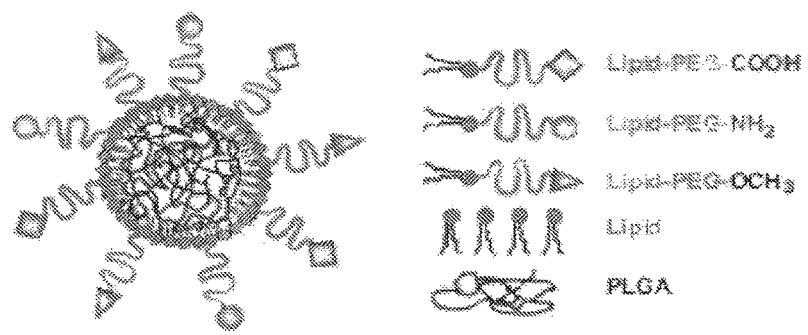
FIG. 5 is a schematic illustration of lipid-polymer (poly (D, L-lactide-co-glycolide))(PLGA) hybrid nanoparticle bearing a mosaic surface pattern of three different functional groups (—COOH, —NH$_2$, and —OCH$_3$). Heterofunctional linker molecules have a lipid-polyethylene glycol (PEG)-functional group form. Thus, there are three different types of heterofunctional linkers, each with a different function group.

One of the new lipid-polymer hybrid particles described herein is illustrated in FIG. 5, and is shown to have three distinct functional groups (COOH, $NH_2$, and $OCH_3$), on its surface. Each of these functional groups can be used to bind to a different targeting moiety. In some aspects, the particles combine characteristics of both liposomes and polymer nanoparticles. They are able to carry poorly soluble drugs and possess high drug carrying capacity. Their circulation half-life is longer than that of polymeric nanoparticles, and a little bit shorter than that of liposomes. This sophisticated and elegant model has a multivalent targeting ability and can be designed to show a sustained drug release. For all these properties lipid-polymer hybrid nanoparticles are ideal candidates to be used as drug delivery vehicles.

In various aspects, the particles according to the present teachings fulfill one or more of the following advantages. First, the particles can be designed as drug delivery vehicles with tremendous variation in the possible active agents and concentrations, thus permitting in certain aspects, the modular design of active agent delivery vehicles. Second, the particles circulate and remain for long periods within an organism, thus avoiding immune system recognition and/or complement activation. Third, active targeting provides the ability to deliver highly specific active ingredients to target tissues (for example, to a tumor site) to minimize systemic effects. This is particularly advantageous for chemotherapeutic treatments for cancer, where damage of attendant tissues can be minimized. Fourth, the particles can be designed to have the ability to release multiple active ingredients with independently controllable release kinetics. In addition, functional imaging can be used to distinguish specific and non-specific binding.

The particles described herein are robust enough to function in a biological environment that includes proteins and cells. In certain aspects, the particles can serve as targeting elements directed to circulating blood cells carrying the active agent payload (e.g., chemotherapy drug) to the tumor. In accordance with the principles of the disclosure, the new methods enable the engineering of spatially separated surface interactions, as well as the establishment of independent release kinetics for respective phases of the particles. These properties can improve active agent delivery.

Moreover, in certain embodiments, each particle can comprise several different targeting moieties. Specifically, the surface functional groups can be selected to be hydrophilic, hydrophobic, positively charged (cationic), negatively charged (anionic), surface active agent modified (e.g., PEG-ylated or covered with a zwitterion), superhydrophobic, superhydrophilic, olephobic, olephilic, and/or nanostructured, as described above. Particles can be designed to have such properties by providing such materials within the material forming the phase, or may be provided by subsequent treating, reacting, or coating of the exposed phase surface after formation of the particle to achieve such properties. Polymers within a particle can further be modified to interact and/or react with certain target moieties. For example, reactive groups on one moiety may be cationic and another moiety may be anionic. In other embodiments, the functional groups of the polymer may participate in a reaction with a functional group present on the targeting moiety, such that they react and are bonded to the surface of the particle. In various aspects, the particles serve as novel drug carriers carrying chemotherapeutics to inhibit or kill cancer cells, but also control drug release; confer immune clearance (most commonly by PEG functionalizing to confer "stealth" properties); and target delivery (by further functionalization with homing molecules to allow selectively binding to cancer cells).

For example nanoparticles can be delivered into a tumor via the passive or active process. In the former, nanoparticles pass through leaky tumor capillary fenestrations into the tumor interstitium and cells by passive diffusion or convection. The latter involves drug delivery to a specific site based on molecular recognition. The most common approach conjugates targeting moieties to the nanoparticles. The targeting moieties enhance the interaction between the nanoparticles and receptors at the target cell site, increasing local drug concentration. Many targeting moieties can be successfully conjugated to the nanoparticles including antibodies, transferrin receptor, folate receptors, and wide range of biomolecules.

Polymers that are biodegradable, biocompatible, have large engineering flexibility, and sustained-release characteristics are the most promising drug delivery carriers. Polymeric nanoparticles, particularly poly (D, L-lactide glycol) (PLGA) based nanoparticles, have been extensively used. To our knowledge, multifunctional nanoparticles based on PLGA conjugated with poly (ethylene glycol) (PEG) are the only system that has been applied in prostate cancer (FIG. 4A). Besides the aforementioned advantages, the PLGA conjugated nanoparticle system is attractive because of PLGA has been approved by the US Food & Drug Administration (FDA), which may facilitate and accelerate the process of reaching clinical trials.

There are other targeting agents, such as nucleic acid ligands, such as aptamers, which are small oligonucleotides that specifically bind to certain target molecules and are potential candidates to target proteins over-expressed in cancer cells, such as prostate cancer cells. A nucleic acid ligand is a nucleic acid that can be used to bind to a specific molecule. For example, pegaptanib is a pegylated anti-VEGF aptamer, a single stranded nucleic acid that binds with high specificity to a particular target. Although the pegaptanib aptamer was originally approved by FDA in 2004 to treat age-related macular degeneration (AMD) disease, it has the potential to treat prostate cancer because it binds specifically to VEGF165, a protein recognized as the key inducer of tumor angiogenesis. Latil et al., Int. J. Cancer., 89(2), 167-171 (2000) suggests that VEGF expression could be used as a prognostic marker in early-stage tumors. Specific aptamers include, for example, Aptamer O-7 which binds to osteoblasts; A10 RNA aptamer, which binds to prostate cancer cells; aptamer TTA1, which binds to breast cancer cells; and the extended A9 RNA aptamer (Javier et al., Bioconjug Chem. 2008 Jun. 18; 19(6):1309-1312). See also, Wilson et al., U.S. Published Patent Application No. 20090105172. In general, aptamers are stable in a wide range of pH (~4-9), physiological conditions, and solvents. Aptamers are known to be less immunogenic than antibodies and can penetrate a tumor more easily because of size. The shape of aptamer binding sites, which includes grooves and clefts, provide highly specific characteristics and drug-like capabilities. Active targeting, however, requires that the RNA aptamers discriminate cancer cells from normal cells.

Other exemplary binding moieties include peptides, such as CLT1 and CLT2, which bind to fibrin-fibronectin complexes in blood clots. Various peptides are well known in the art for binding to cells in the brain, kidneys, lungs, skin, pancreas, intestine, uterus, adrenal gland, and prostate, including those described in Pasqualini et al., Mol. Psychiatry, 1(6):421-2 (1996) and Rajotte et al., J. Clin. Invest., 102(2):430-437 (1998), for example.

In one aspect of the invention, the multifunctional particles can be modified by transcriptional targeting. Transcriptional targeting is a gene therapy method, which refers to the use of particular cell-specific regulatory elements (promoters or promoter/enhancers) to restrict gene expression to a particular tissue or cell type. Nonviral vectors like nanoparticles have shown success of in vivo gene delivery. Chumakova et al., Cancer Lett., 261(2), 215-225 (2008) describes the use of ultrasound with nanoparticles to enhance drug and gene delivery in prostate cancer cells in vivo because ultrasound alters properties of tumor vasculature and the cell membrane. Multifunctional nanoparticles reported for gene delivery in prostate cancer include multivalent cations like polyamines, PEI, and peptides like poly-L-lysine, which help condense DNA during gene delivery. See, e.g., De Smedt et al., Pharm Res., 17(2), 113-126 (2000). Depending on their molecular weights, PEI is known to help disrupt the endosomal membrane and enhance gene delivery. See, e.g., Prabha et al., Pharm Res. 21(2), 354-364 (2004). Hattori et al., Biol. Pharm. Bull., 30(9), 1773-1778 (2007) describes combining PET with cationic cholesterol derivatives to increase transfection efficiency.

In one aspect of the invention, there may be two or more distinct target moieties bound to the surface of a particle. A primary target can be an immune system cell, such as a leukocyte or T-cell, and a secondary target can be a malignant cancer cell(s) within a tumor, which is the target region. The moiety on the surface of particle binds to the primary target cell with high selectivity, while the second moiety has a general tumor targeting surface domain. Suitable moieties for binding with targets associated with an animal include those described herein. Thus, after delivery of the inventive multifunctional particles to the target tissue, the particles having tumor targeting moieties can bind with the secondary target (e.g., cancer) cells, once they detach from originally targeted cells. In certain aspects, a particle delivery system is provided for active agent delivery that is long-circulating, highly selective, and enables the release of multiple drugs with complex release kinetics.

Other targeting moieties include agents that specifically bind to biological targets such as a particular immune system cell (e.g., a T cell or B cell), a protein, an enzyme, or other circulating agent associated with a subject. The following provides are exemplary and non-limiting examples of suitable targeting moieties for use with the multifunctionalized particles described herein. Proteins, such as heat shock protein HSP70 for dendritic cells and folic acid to target cancer cells. Polysaccharides or sugars, such as silylic acid for targeting leucocytes, targeting toxins such as saporin, antibodies, including CD 2, CD 3, CD 28, T-cells, and other suitable antibodies are listed in a Table available on the internet on the World Wide Web at "researchd.com/rdicdabs/cdindex.htm," incorporated herein by reference.

The term "binding," as used herein, refers to the interaction between a corresponding pair of molecules or portions thereof that exhibit mutual affinity or binding capacity, typically due to specific or non specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to binding by molecules, such as polynucleotides, antibodies, and other ligands, that are able to bind to or recognize a binding partner (or a limited number of binding partners) to a substantially higher degree than to other, similar biological entities. In one set of embodiments, the targeting moiety has a specificity (as measured via a disassociation constant) of less than about 1 micromolar, at least about 10 micromolar, or at least about 100 micromolar.

Non-limiting examples of biological moieties include a peptide, a protein, an enzyme, a nucleic acid, a fatty acid, a hormone, an antibody, a carbohydrate, a peptidoglycan, a glycopeptide, or the like. These and other biological moieties are discussed in detail below. In some cases, the biological targeting moiety may be relatively large, for example, for peptides, nucleic acids, or the like. For example, the biological moiety may have a molecular weight of at least about 1,000 Da, at least about 2,500 Da, at least about 3000 Da, at least about 4000 Da, or at least about 5,000 Da, etc. Relatively large targeting moieties may be useful, in some cases, for differentiating between cells. For instance, in some cases, smaller targeting moieties (e.g., less than about 1000 Da) may not have adequate specificity for certain targeting applications, such as targeting applications. In contrast, larger molecular weight targeting moieties can offer a much higher targeting affinity and/or specificity. For example, a targeting moiety may offer smaller dissociation constants, e.g., tighter binding. However, in other embodiments, the targeting moiety may be relatively small, for example, having a molecular weight of less than about 1,000 Da or less than about 500 Da.

In one embodiment, the targeting moiety includes a protein or a peptide. "Proteins" and "peptides" are well-known terms in the art, and are not precisely defined in the art in terms of the number of amino acids that each includes. As used herein, these terms are given their ordinary meaning in the art. Generally, peptides are amino acid sequences of less than about 100 amino acids in length, but can include sequences of up to 300 amino acids. Proteins generally are considered to be molecules of at least 100 amino acids. A protein may be, for example, a protein drug, an antibody, an antibody fragment, a recombinant antibody, a recombinant protein, an enzyme, or the like. In some cases, one or more of the amino acids of the protein or peptide may be modified in some instances, for example, by the addition of a chemical entity such as a carbohydrate group, a phosphate group, a farnesyl group, an isofarnesyl group, a fatty acid group, a linker for conjugation, functionalization, or other modification, etc.

Other examples of peptides or proteins include, but are not limited to, ankyrins, arrestins, bacterial membrane proteins, clathrin, connexins, dystrophin, endothelin receptor, spectrin, selectin, cytokines; chemokines; growth factors, insulin, erythropoietin (EPO), tumor necrosis factor (TNF), neuropeptides, neuropeptide Y, neurotensin, transforming growth factor alpha, transforming growth factor beta, interferon (IFN), and hormones, growth inhibitors, e.g., genistein, steroids etc; glycoproteins, e.g., ABC transporters, platelet glycoproteins, GPIb-IX complex, GPIIb-IIIa complex, vitronectin, thrombomodulin, CD4, CD55, CD58, CD59, CD44, CD168, lymphocye function-associated antigen, intercellular adhesion molecule, vascular cell adhesion molecule, Thy-1, antiporters, CA-15-3 antigen, fibronectins, laminin, myelin-associated glycoprotein, GAP, and GAP43. Other examples include affibodies, nanobodies, avimers, adnectins, domain antibodies, and small modular immunopharmaceuticals (SMIP™)(Trubion Pharmaceuticals Inc., Seattle, Wash.).

As used herein, an "antibody" refers to a protein or glycoprotein consisting of one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well characterized fragments produced by digestion with various peptidases.

Non-limiting examples of antibodies and other suitable targeting moieties include anti-cluster of differentiation antigen CD-1 through CD-166 and the ligands or counter receptors for these molecules; anti-cytokine antibodies, e.g., anti-IL-1 through anti-IL-18 and the receptors for these molecules; anti-immune receptor antibodies, antibodies against T cell receptors, major histocompatibility complexes I and II, B cell receptors, selectin killer inhibitory receptors, killer activating receptors, OX-40, MadCAM-1, GlyCAM1, integrins, cadherens, sialoadherens, Fas, CTLA-4, Fc-gamma receptor, Fc-alpha receptors, Fc-epsilon receptors, Fc-mu receptors, and their ligands; anti-metalloproteinase antibodies, e.g., collagenase, MMP-1 through MMP-8, TIMP-1, TIMP-2; anti-cell lysis/proinflammatory molecules, e.g., perforin, complement components, prostanoids, nitrous oxide, thromboxanes; or anti-adhesion molecules, e.g., carcioembryonic antigens, lamins, or fibronectins.

Other examples of targeting moieties include cytokines or cytokine receptors, such as Interleukin-1 (IL-1), IL-2, IL-3, IL-4, IL-5, IL-6, IL-7, IL-8, IL-9, IL-10, IL11, IL-12, IL-13, IL-14, IL-15, IL-16, IL-17, IL-18, IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, lymphokine inhibitory factor, macrophage colony stimulating factor, platelet derived growth factor, stem cell factor, tumor growth factor beta, tumor necrosis factor, lymphotoxin, Fas, granulocyte colony stimulating factor, granulocyte macrophage colony stimulating factor, interferon alpha, interferon beta, interferon gamma.

Still other examples of targeting moieties include growth factors and protein hormones, for example, erythropoietin, angiogenin, hepatocyte growth factor, fibroblast growth factor, keratinocyte growth factor, nerve growth factor, tumor growth factor alpha, thrombopoietin, thyroid stimulating factor, thyroid releasing hormone, neurotrophin, epidermal growth factor, VEGF, ciliary neurotrophic factor, LDL, somatomedin, insulin growth factor, or insulin-like growth factor I and II.

Additional examples of targeting moieties include chemokines, for example, ENA-78, ELC, GRO-alpha, GRO-beta, GRO-gamma, HRG, LIF, IP-10, MCP-1, MCP-2, MCP-3, MCP-4, MTP-1 alpha, MIP-1 beta, MIG, MDC, NT-3, NT-4, SCF, LIF, leptin, RANTES, lymphotactin, eotaxin-1, eotaxin-2, TARC, TECK, WAP-1, WAP-2, GCP-1, GCP-2, alpha-chemokine receptors such as CXCR1, CXCR2, CXCR3, CXCR4, CXCR5, CXCR6, CXCR7, or beta-chemokine receptors such as CCR1, CCR2, CCR3, CCR4, CCR5, CCR6, or CCR7.

In another embodiment, the targeting moiety includes a nucleic acid. The term "nucleic acid," or "oligonucleotide," as used herein, refers to a polymer of nucleotides. As used herein, a "nucleotide" is given its ordinary meaning as used in the art, i.e., a molecule comprising a sugar moiety, a phosphate group, and a base (usually nitrogenous). Typically, the nucleotide comprises one or more bases connected to a sugar-phosphate backbone (a base connected only to a sugar moiety, without the phosphate group, is a "nucleoside"). The sugars within the nucleotide may be, for example, ribose sugars (a "ribonucleic acid," or "RNA"), or deoxyribose sugars (a "deoxyribonucleic acid," or "DNA"). In some cases, the polymer may comprise both ribose and deoxyribose sugars. Examples of bases include, but not limited to, the naturally-occurring bases (e.g., adenosine or "A," thymidine or "T," guanosine or "G," cytidine or "C," or uridine or "U"). In some cases, the polymer may also comprise nucleoside analogs (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, Ml-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, 2-thiocytidine, etc.), chemically or biologically modified bases (e.g., methylated bases), intercalated bases, modified sugars (e.g., 2'-fluororibose, 2'-aminoribose, 2'-azidoribose, 2'-O-methylribose, L-enantiomeric nucleosides arabinose, hexose, etc.), modified phosphate moieties (e.g., phosphorothioates or 5'-N-phosphoramidite linkages), and/or other naturally and non-naturally occurring bases substitutable into the polymer, including substituted and unsubstituted aromatic moieties. Other suitable base and/or polymer modifications are well-known to those of skill in the art. In some cases, the polynucleotide may include DNA, RNA, modified DNA, modified RNA, antisense oligonucleotides, expression plasmid systems, nucleotides, modified nucleotides, nucleosides, modified nucleosides, intact genes, or combinations thereof. Other examples of polynucleotides include interfering RNA, natural or unnatural siRNAs, shRNAs, microRNAs, ribozymes, DNA plasmids, antisense oligonucleotides, randomized oligonucleotides, or ribozymes.

These prostate cancer targeted particles can be delivered into the tumor via the passive or active process. In the former, nanoparticles pass through leaky tumor capillary fenestrations into the tumor interstitium and cells by passive diffusion or convection. The latter involves drug delivery to a specific site based on molecular recognition. The most common approach conjugates targeting ligands to the nanoparticles. The targeting ligands enhance the interaction between nanoparticles and receptors at the target cell site, increasing local drug concentration. Many ligands have been successfully conjugated to the nanoparticles including antibodies, transferrin receptor, folate receptors, and wide range of biomolecules, as discussed above.

Examples of molecules targeting extracellular matrix ("ECM") include glycosaminoglycan ("GAG") and collagen. The outer surface of the particles that have a carboxy functional group can be linked to Pathogen-associated molecular patterns (PAMPs) that have a free amine terminus. The PAMPs target Toll-like Receptors (TLRs) on the surface of the cells or tissue, or signals the cells or tissue internally, thereby potentially increasing uptake. PAMPs conjugated to the particle surface or co-encapsulated can include: unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2

(bacterial), flagellin (bacterial) poly(inosinic-cytidylic)acid (bacterial), lipoteichoic acid (bacterial) or imidazoquinolines (synthetic).

In another embodiment, the outer surface of the particle can be treated using a mannose amine, thereby mannosylating one domain in the mosaic surface pattern. This treatment causes the particle to bind to the target cell or tissue at a mannose receptor on an Antigen Presenting Cell surface. Alternatively, surface conjugation with an immunoglobulin molecule containing an Fc portion (targeting Fc receptor), heat shock protein moiety (HSP receptor), phosphatidylserine (scavenger receptors), and lipopolysaccharide (LPS) are additional receptor targets on cells or tissue.

Lectins can also be used as targeting moieties that can be covalently attached to the linkers of the new particles to target them to the mucin and mucosal cell layers. Such lectins can be isolated from *Abrus precatroius, Agaricus bisporus, Anguilla anguilla, Arachis hypogaea, Pandeiraea simplicifolia, Bauhinia purpurea, Caragan arobrescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus, Lysopersicon esculentum, Maclura pomifera, Momordica charantia, Mycoplasma gallisepticum, Naja mocambiquc*, as well as the lectins Concanavalin A, Succinyl-Concanavalin A, *Triticum vulgaris, Ulex europaeus* I, II and III, *Sambucus nigra, Maackia amurensis, Limax fluvus, Homarus americanus, Cancer antennarius*, and *Lotus tetragonolobus*.

Additional targeting moieties are described in PCT WO 2008, 124632, which is incorporated herein by reference in its entirety. Other targeting moieties known or to be developed in the art are contemplated for use with the present disclosure.

Methods of Use of Multifunctional Particles

The new particles can be used in a wide variety of diverse methods as described in further detail below. However, the descriptions below are not meant to limit the scope of the invention as described in the claims.

Biodegradable Multifunctional Particles for Controlled and/or Sustained Release

In certain aspects, the particles dissolve or disintegrate at different rates. In this regard, the dissolution rate of the particle impacts the release rate of the active agent, thus providing control over the release kinetics and concentration of active agent to be delivered to target regions. As referred to herein, "dissolve" refers to physical disintegration, erosion, disruption and/or dissolution of a material. The phases may dissolve or disintegrate at different rates or have different solubilities (e.g., aqueous solubility) that impact the rate of active agent release. Particles comprise one or more materials that dissolve or erode upon exposure to a solvent comprising a high concentration of water, such as serum, blood, bodily fluids, or saliva. In some variations, a particle may disintegrate into small pieces or may disintegrate to collectively form a colloid or gel. In some aspects, a phase of the particle comprises a polymer that is insoluble or has limited solubility in water, but is dispersible in water, so that the polymer breaks down or erodes into small fragments. In other aspects, a polymer used in a phase of the particle is insoluble in water, but swellable. In variations where a polymer does not fully break down during use, the polymer can be a water-repellant polymer or an aqueous-stable hydrophilic polymer, for example, certain types of cellulose. In various aspects, each phase of the MPN optionally comprises a combination of polymer materials.

Research and development in the field indicates biodegradable and low immunogenic particles will have a great impact on the fight against various disorders, such as cancer, as drug carriers and molecular probes or diagnostic devices. It is important to note that the non-homogeneous delivery of therapeutic agents to tumors using these particles delivery systems may lead to ineffective drug efficacy for drugs which intracellular delivery is required for bioactivity (example: siRNA); additionally non-homogenous drug delivery may enhance the emergence of chemotherapeutic drug resistance. There are currently an increasing number of particle designs being developed for combination-drug therapy, enhanced tumor penetration and effective intracellular delivery (example: targeted lipid-polymer hybrid particles) that might maximize the therapeutic effectiveness of drugs which need intracellular delivery, while minimizing drug resistance problems common to anticancer agents. PLGA and PLA are other polymers of special interest in gene delivery due to their biocompatibility, biodegradability and sustained-release characteristics and may be used in certain aspects of the invention.

In one embodiment, the directional release of a drug active agent loaded into one of the new particles can be used to selectively deliver a drug in a very precise location while limiting a systemic delivery. For example, a particle can be designed to have a first functional group that is hydrophobic in one hemisphere of an external mosaic pattern, and a second functional group that is hydrophilic in the other hemisphere. The particle is further designed to have a targeting agent bound to the hydrophobic functional group to target the particle to a specific biological target, such as an endothelial cell of a blood vessel wall. If a hydrophobic drug is loaded into the core structure of this particle, it will tend to be released through the side of the particle that has the hydrophobic functional groups. Thus, when the particle is administered systemically, it will reach and bind to its target cell, and then release the drug asymmetrically to the target cell, and not into the surrounding blood in the blood vessel, thereby limiting a systemic release of the drug.

Multifunctional Particles in Therapeutic, Pharmaceutical, Cosmetic, and Personal Care Applications In certain aspects, particles can be provided in pharmaceutical compositions. In certain pharmaceutical compositions, the active agent is provided in a suitable pharmaceutical excipient, as are well known in the art. Thus, administration of the particles in a pharmaceutical composition can be, for example, intravenous, topical, subcutaneous, transcutaneous, intramuscular, oral, intra-joint, parenteral, peritoneal, intranasal, by inhalation, e.g., pulmonary delivery, or within or coating a medical device or implant. Pharmaceutical compositions are optionally provided in the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, in unit dosage forms suitable for administration of precise dosages.

As discussed above, certain suitable active ingredients for pharmaceutical compositions or nutritional compositions, are known to those of skill in the art and include, but are not limited to, low-molecular weight molecules, quantum dots, natural macromolecules, such as proteins, sugars, peptides, DNA, RNA, and the like, artificial macromolecules, polymers, dyes and colorants, inorganic ingredients including nanomaterials and nanocrystals, fragrances, and mixtures thereof. By way of non-limiting example, the active ingredient can be a therapeutic drug that operates locally or systemically (non-localized) and may treat, prevent, or diagnose a wide variety of conditions or ailments. Active agents may be used to treat or prevent a disease, such as an infectious disease (a bacterial, viral, or fungal infection) or a degenerative disease (Alzheimer's, amyotrophic lateral sclerosis (ALS)). For example, active agents may treat an auto-immune disorder (e.g., rheumatoid arthritis, systemic lupus erythematosus (SLE), inflammatory bowel disease (IBD)), allergies, asthma, osteoarthritis, osteoporosis, cancer, diabetes, arteriosclerosis and cardiovascular disease, stroke, seizures, psychological disorders, pain, acne, caries, gingivitis, periodontitis, an $H_2$ antagonist, and the like. Various suitable active agents or ingredients are disclosed in Merck Index, An Encyclopedia of Chemicals, Drugs, and Biologicals, Thirteenth Edition (2001) by Merck Research Laboratories and the International Cosmetic Ingredient Dictionary and Handbook, Tenth Ed., 2004 by Cosmetic Toiletry and Fragrance Association, and U.S. Pat. Nos. 6,589,562; 6,825,161; 6,063,365; and 6,491,902, all to Shefer et al.

Furthermore, in other aspects multifunctional particles can be used in personal care compositions, such as soaps, bath gels, body washes, exfoliating scrubs, shampoos, lotions, serums, creams, sunscreens, self-tanning products, antiperspirant and deodorant products, nail care products, cosmetics, and the like. For personal care and cosmetic compositions, suitable active ingredients include anti-oxidants; free radical scavengers; moisturizers; depigmentation agents; skin lightening agents; reflectants; humectants; antimicrobial agents; antibacterial agents; allergy inhibitors; anti-acne agents; anti-aging agents; anti-wrinkling agents, antiseptics; analgesics; keratolytic agents; anti-inflammatory agents; fresheners; healing agents; anti infective agents; inflammation inhibitors; wound healing promoters; peptides, polypeptides; proteins; deodorants; antiperspirants; skin emollients; skin moisturizers; tanning agents; skin lightening agents; antifungals; depilating agents; counterirritants, non-steroidal soothing agents, anti-itch agents, poison ivy agents; poison oak agents; burn products; make-up preparations; vitamins; amino acids and their derivatives; herbal extracts; cooling agents; heating agents; skin conditioners; chelating agents; cell turnover enhancers; coloring agents; sunscreens; nourishing agents; moisture absorbers; sebum absorbers; skin penetration enhancers, pigments, dyes, fragrances, and the like, such as those disclosed in U.S. Pat. No. 6,825,161 to Shefer et al.

As described above, various active ingredients are well known to those of skill in the art and include those outlined in the International Cosmetic Ingredient Dictionary and Handbook, referenced above. Various suitable active agents or ingredients are known to those of skill in the art.

For use in wound healing, particles can be designed to have a first functional group bound to a targeting agent that specifically binds to collagen, such as collagen binding peptides, and a second functional group bound to an antimicrobial. A third functional group could be bound to a growth factor (or either the antimicrobial or growth factor could be loaded into the core structure of the particle. Other active agents include growth factors such as epidermal growth factor, transforming growth factors, hepatocyte growth factor, platelet-derived growth factor, vascular endothelial growth factor, fibroblast growth factors, and keratinocyte growth factor.

For use after angioplasty, the new particles can be functionalized and targeted to bind specifically to the endothelial cells on the vascular walls, which have been damaged by the angioplasty procedure. The particles also are loaded with, or bound to, PEG to form a protective layer to block platelets from sticking and forming clots, as well as rapamycin, to block restenosis. The new particles uniquely enable the precise delivery of two, three, or more such active agents.

For use in the eye, particles are designed to include a targeting agent that binds to the surface of the cornea, and an active agent attached to a second functional group or loaded into the particle to provide hydration to the eye, e.g., by including a steroid or a purinergic receptor agonist (see, e.g., U.S. Pat. No. 6,696,425, which is incorporated herein by reference in its entirety). This is an effective therapy against dry eye syndrome.

For use in vaccine compositions, the new particles are designed so that a first functional surface domain includes a targeting agent that binds to antigen presenting cells ("APC")(e.g., B-cells, dendritic cells, and macrophages), e.g., macrophages that display CD168. A second functional surface domain is bound to an antigen. When administered, the new particles thus provide a much more directed presentation of the antigen to the APC than occurs with normal vaccines, which merely rely on random chance for the APCs to bind to the desired antigen. See also, von Andrian et al., Vaccine Nanotechnology, WO 2009/051837, which is incorporated herein by reference in its entirety. These vaccine particles can be administered to selectively enter the subcapsular sinus of the lymph nodes (e.g., under two-photon microscopy imaging), and thus be preferentially bound to macrophages located in this region.

In addition, the particles can also include known antigens and/or adjuvants bound to a surface functional group. Examples of commonly used adjuvants in vaccine preparations include aluminum potassium sulfate, Freund's incomplete adjuvant, Freund's complete adjuvant, alum, synthetic ribonucleotides, and bacterial lipopolysaccharides.

The new particles can also be used to deliver DNA vaccines. Cell-mediated immunity is needed to detect and destroy virus-infected cells. Most traditional vaccines (e.g. protein-based vaccines) can only induce humoral immunity. DNA-based vaccines represent a unique means to vaccinate against a virus or parasite because a DNA based vaccine can induce both humoral and cell-mediated immunity. In addition, DNA-based vaccines are potentially safer than traditional vaccines. DNA vaccines are relatively more stable and more cost-effective for manufacturing and storage. DNA vaccines consist of two major components—DNA carriers (or delivery vehicles) and DNAs encoding antigens. DNA carriers protect DNA from degradation, and can facilitate DNA entry to specific tissues or cells and expression at an efficient level. The new particles can be designed to target the particles to a specific tissue (with a targeting agent bound to a first functional group on the surface), and the desired DNA vaccine can be loaded within the core structure to protect the DNA during delivery to the target tissue. Adjuvants can also be bound to a second functional group on the surface of the particles.

For complement activation, a particle can be designed so that one of the surface functional groups is bound to a complement activation molecule, such as C3a, and another of the surface functional groups is bound to the desired antigen. In general, the more negative the surface charge of the external mosaic pattern on the new particles, the more the particles tend to activate the complement system. For example, a methoxyl functional group tends to minimally activate the complement system. The use of amine surface functional groups tends to induce the highest level of activation. By selecting various functional groups, one can activate the complement system to varying degrees and along various pathways. Thus, the present disclosure includes methods of modulating the human complement system via the combination of multiple pairs or triplets (or more) of different functional groups, as well as methods of manipulating key complement proteins such as Factor H and C3b via such functional groups. See also the examples herein, which show that particles with methoxyl functional groups are ideal candidates for drug delivery, because they are not likely to cause any immunologically adverse reactions in the human body. See also, Salvador-Morales et al., Biomaterials, 30:2231-2240 (2009), which is incorporated herein by reference in its entirety.

In another embodiment, the new particles can be used to inhibit wound adhesion that often occurs after surgery, e.g., intra-abdominal surgery. The problem is that as the surgical cuts and nicks of the abdominal wall heal, they tend to bind together, and thus tissues that should not be connected can become connected by the newly forming tissue. The new particles can be designed with one surface functional group, e.g., a maleimide group, can be bound to a collagen binding peptide or other targeting agent that binds the extracellular matrix that is exposed during surgery. Another surface functional group, such as an amino or methoxyl group, is bound to a hydrophobic molecule, such as PEG or PEO to form an anti-fouling surface coating over the wound, to prevent tissues from different areas from healing together. The particles would be applied to the surfaces after surgery, and the core structures would be made with biodegradable polymers so that they dissolve over time, once the wound has fully healed. In addition, these particles could be loaded with or bound to healing factors, such as the growth factors described herein.

In other aspects, a multifunctional particle having an active agent can be used in an oral care composition, which can be in the form of a dentifrice, such as toothpastes, toothpowders, and prophylaxis pastes, confectioneries, including gums, beads and chews, films, paint-on products, professional polishing formulations or any other form known to one of skill in the art. Selection of specific carrier components is dependant on the desired product form, including dentifrices, toothpastes, tooth powders, prophylaxis pastes, mouth rinses, lozenges, gums, gels, paints, medicaments, and the like.

Non-limiting examples of oral care active ingredients among those useful in a particle for use in an oral care composition include anti-plaque agents, anti-gingivitis agents, antimicrobial agents, anti-tartar agents, anti-caries agents, anti-viral agents, anti-inflammatory agents, antioxidants, whitening agents, desensitizing agents, vitamins, nutrients, natural extracts and essential oils, compatible enzymes, periodontal actives, breath freshening agents, malodor control agents, salivary stimulants, pH modifying agents, analgesics and combinations and mixtures thereof. Other oral active ingredients among those useful herein are also disclosed in U.S. Pat. No. 6,685,921 to Lawlor; U.S. Pat. No. 6,132,702 to Witt et al., and U.S. Pat. No. 5,741,138 to Rice et al.

In the area of hair care, many products are known to curl hair, or to prevent curling. In one example, particles can be designed with a targeting agent that binds specifically and strongly to proteins on hair shafts, e.g., keratin through keratin-binding peptides attached to a first functional group such that once the particles bind to hair (e.g., when applied in a gel, spray, shampoo, conditioner, or mousse), they form a coating that inhibits moisture from causing the hair to curl or frizz. For example, polyfluoroester compositions can be used with the new particles.

Multifunctional Particles in Food, Beverages, and Nutritional Supplements

In certain aspects, the particles can be used in exemplary nutritional compositions, such as food, drinks, pills, and supplements. Suitable active agents include those that are nutrients, such as vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), fish oil (including components thereof such as omega-3 (N-3) polyunsaturated fatty acids, eicosapentaenoic acid and docosahexaenoic acid), coenzyme Q10, and mixtures thereof. Other useful active ingredients are neutraceuticals such as vitamin E, folate, acetyl-L-carnitine (AL-CAR), N-acetyl cysteine (NAC), S-adenosyl methionine (SAM), and 3-deazaadenosine (DZA). These formulations are said to inhibit the progressive loss of neurons in neurodegenerative disorders such as Alzheimer's disease and Parkinson's disease, as well as normal aging.

Multifunctional Particles in Diagnostics

In still another set of embodiments the new particles described herein can include an imaging agent or a sensing agent, i.e., a moiety that can be determined in some fashion, either directly or indirectly. For instance, the imaging agent may be fluorescent, radioactive, electron-dense, a member of a binding pair, a substrate for an enzymatic reaction, an antigen for an antibody, etc. In some cases, the imaging entity itself is not directly determined, but instead interacts with a second entity in order to effect determination; for example, coupling of the second entity to the imaging entity may result in a determinable signal. Non-limiting examples of imaging moieties includes fluorescent compounds such as FITC or a FITC derivative, fluorescein, GFP, etc.; a radioactive atom, for example, 3H, 14C, 33P, 32P, 125I, 131I, 35S, etc.; or a heavy metal species, for example, gold or osmium. As a specific example, an imaging moiety may be a gold nanoparticle.

For example, the active agent of the particle in the disclosure may be used for diagnostic purposes, such as in various diagnostic medical imaging procedures (for example, radiographic imaging (x-ray), fluorescence spectroscopy, Forster/fluorescent resonance energy-transfer (FRET), computed tomography (CT scan), magnetic resonance imaging (MRI), positron emission tomography (PET), other nuclear imaging, and the like). Active agents for use with diagnostic imaging include contrast agents, such as barium sulfate, gadolinium, or metal oxides, such as iron oxide particles, for use with MRI, or, for example, fluorescein isothiocyanate (FITC) for fluorescent scans.

In addition, because of the unique properties of the new particles, two, three, four, or more different imaging agents can be bound to different functional groups in the external mosaic patterns. For example, particles with two different surface domains can be used as switchable particles that are bound to two different imaging agents, such as dyes, and can be independently bound to a targeting agent and/or loaded with a drug or other active agent as well. When the particles bind to a surface or to other particles, they self-orient in a way that displays a visible color change upon binding.

Multifunctional Particles in Medical Devices

Medical devices and/or implants, such as a stent, a pacemaker, a pacemaker lead, a defibrillator, a drug delivery device, a sensor, a pump, an embolization coil, a clip, a suture, or an electrode, by way of example, can include multifunctional particles having an active ingredient according to the present disclosure. Exemplary medical implants include stem tissue grafts, tissue scaffolds, organ transplants, genetic therapy or stem cell therapy, among others. Where a particle is used in an implant or in conjunction with a medical device or transplant, a variety of active ingredients can be employed to promote healing, such as promoting growth and reducing inflammation. Notwithstanding those ingredients already discussed, other active ingredients include by way of example, growth hormones and growth factors, like bone morphogenic protein (BMP) or cartilage transcription factor SRY-related HMG-box gene 9 (Sox-9)); anti-rejection drugs (such as cyclosporine), anti-inflammatory agents, analgesics, stem cell or gene therapies, or other agents that promote healing, including anti-oxidants, free radical scavengers, nutrients, co-enzymes, and other bio-functional compounds or active ingredients known or to be developed for use in such applications by those of skill in the art. Further, compositions having such active agents can be used in conjunction with wound dressings, gauze, films, and the like.

Multifunctional Particles for Industrial and Agricultural Uses

In alternate variations, the particles can be used in cleansers and/or home care compositions including powders, pastes, dishwashing liquids and automatic dishwasher detergents, fabric detergents and softeners, and hard surface cleansers. Active agents include enzymes, bleaching agents, surface active agents, phosphates, builders, and the like.

The new particles can also be used in agricultural compositions including fertilizers, pesticides, fungicides, rodenticides, insecticides, and the like. In particular, the new particles permit the delivery, e.g., to roots or leaves, of both fertilizers and pesticides, in a controlled and highly specific manner. Magnetic (iron oxide) nanoparticles can also help to visualize plant tissue. The same principles in medical use can be applied for a broad range of uses in plants, in particular to tackle infections. Nanoparticles tagged to agro-chemicals or other substances can reduce the damage to other plant tissues and the amount of chemicals released into the environment.

EXAMPLES

The invention is further described in the following examples, which do not limit the scope of the invention described in the claims.

Example 1

Preparation of Nanoparticles with One Functional Surface Domain

Firstly, we prepared lipid-polymer hybrid nanoparticles using a linker containing only one functional group, e.g., an amine group. Poly (D, L-lactide-co-glycolide)-Lipid poly (ethylene glycol) nanoparticles (PLGA-Lipid-PEG particles) were prepared using the following protocol. PLGA polymer was dissolved in acetonitrile at a concentration of 2 mg/mL. The lipid lecithin (Alfa Aesar) was mixed with 1, 2-Distearoyl-sn-Glycero-3-Phosphoethanolamine-N-[Carboxy (Polyethylene Glycol) 2000] (DSPE-PEG-COOH) (Avanti Polar Lipids) at a molar ratio of 8.5:1.5 and dissolved in 4% ethanol aqueous solution. The total lipid weight (lecithin+DSPE-PEG-COOH) was 15% of the PLGA polymer. The lipid solution was preheated at 65° C. for 3 minutes, and the PLGA solution was added dropwise under gentle stirring. The mixed solution was vortexed vigorously for 3 minutes followed by gentle stirring for 2 hours at room temperature. Finally the nanoparticles were washed three times using an Amicon Ultra-4 centrifugal filter (Millipore, Billerica, Mass.) with a molecular weight cutoff of 10K Da.

Figure 6A:
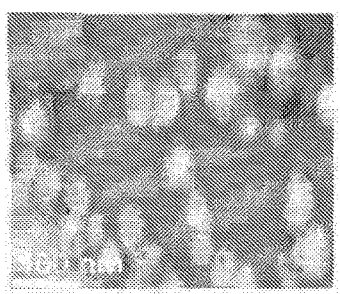
FIGS. 6A, 6B, and 6C are various transmission electron microscope images (taken at 80 kV acceleration voltage) of the localization of the functional groups distributed on the surface of PLGA-lecithin-PEG nanoparticles functionalized with only NH$_2$.
Figure 6B:
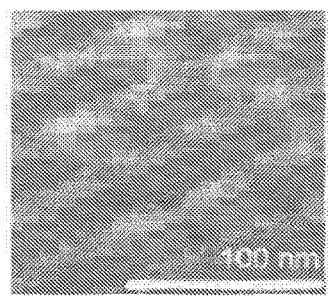
Figure 6C:
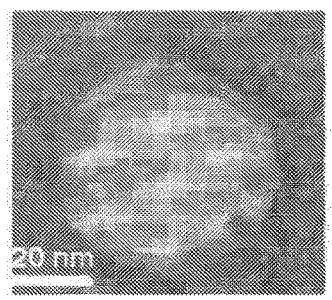

Lipid-polymer hybrid nanoparticles with amine groups were coupled with carboxylated quantum dots of 5 nm diameter (quantum dots were used as tracking molecules). The cross section of a transmission electron microscope image revealed the presence of quantum dots on the surface of the nanoparticles, FIGS. 6A, 6B, and 6C. Particles are shown at different magnification, 100 nm, 20 nm, and 50 nm, respectively. TEM images were obtained using a 1200 (JEOL, JAPAN) with an accelerating voltage of 80 kV. Nanoparticles were loaded on a copper grid and stained with uranyl acetate.

These results show that the particles functionalized by amine groups only are homogeneously distributed along the surface of the particle.

Example 2

Preparation of Nanoparticles with Multiple Different Functional Groups

To synthesize segregated hemispheres, we used two different functional groups intercalated in 50% molar ratio in the polymer heart of the hybrid nanoparticle. Lipid-polymer hybrid nanoparticles with multiple functionalized surface domains were prepared by functionalizing half of PLGA-Lecithin-PEG nanoparticles with 50% $NH_2$ and 50% methoxyl or maleimide surface functional groups in FIG. 7A-7C (with methoxyl) and FIG. 8A-8D (with malemide). PLGA-Lecithin-PEG-$NH_2$ were suspended in water and incubated with NHS and EDC for 30 minutes. Particles were then washed three times with MQ water by ultrafiltration. The NHS-activated particles were resuspended in PBS and reacted with carboxylated quantum dots for 1 hour. The resulting PLGA-Lecithin-PEG-$NH_2$-QDts bioconjugate was washed three times with MQ water by ultrafiltration. Besides ultrafiltration, some excess of quantum dots was further removed by pipetting out the supernatant during the third wash before re-suspending the nanoparticle pellets.

Immediately PLGA-Lecithin-PEG-$NH_2$-QDts particles were resuspended in 1 ml of PBS, pH 7.4. Gold nanoparticles were added to the nanoparticles and incubated for 2 hours followed by three washes. Samples of polymeric nanoparticles with multiple functionalized surface domains were examined with transmission electron microscope. TEM images were obtained using a 1200 (JEOL, JAPAN) with an accelerating voltage of 80 kV. Nanoparticles were loaded on a copper grid and stained with uranyl acetate.

Figure 7A:
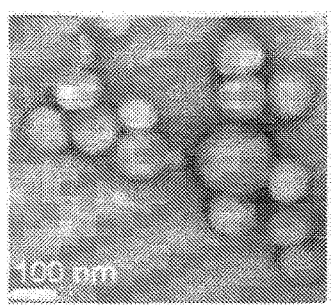
FIGS. 7A, 7B, and 7C are transmission electron microscope images (taken at various acceleration voltages; 80 kV (FIG. 7A), 100 kV (FIG. 7B) and, 80 kV (FIG. 7C)) of the localization of functional groups distributed on the surface of PLGA-Lecithin-PEG nanoparticles functionalized with 50% NH$_2$ and 50% OCH$_3$.
Figure 7B:
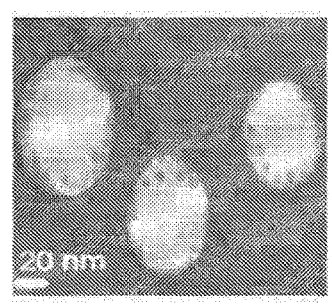
Figure 7C:
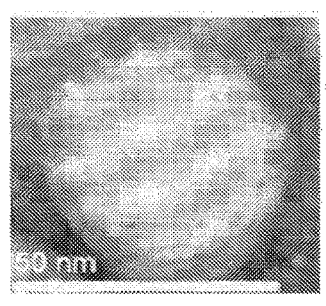
Figure 8A:
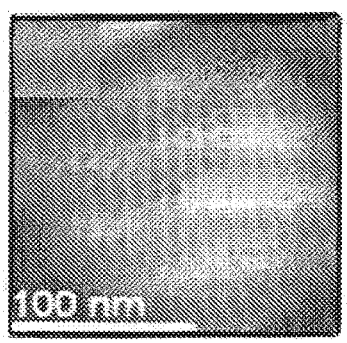
FIGS. 8A, 8B, 8C and 8D are various transmission electron microscope images (taken at acceleration voltages of 80 kV (FIGS. 8A, 8B, 8D) and 50 kV (FIG. 8C)) of the localization of functional groups distributed on the surface of lipid-polymer nanoparticles functionalized with 50% NH$_2$ and 50% maleimide.
Figure 8B:
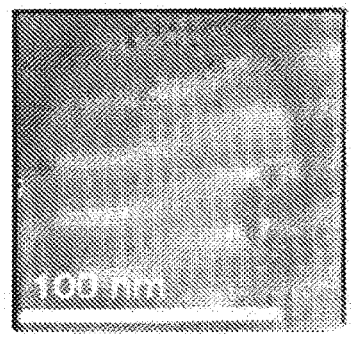
Figure 8C:
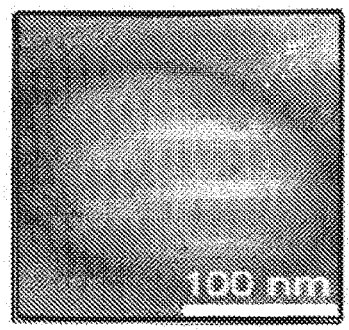
Figure 8D:
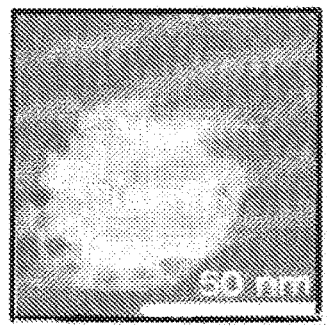

FIGS. 7A, 7B, and 7C show images of lipid-polymer hybrid nanoparticles functionalized with 50% amine and 50% methoxyl. The surface terminal amine group of the particle was labeled with quantum dots, while the remaining methoxyl groups were not labeled. FIGS. 7A, 7B, and 7C clearly show the presence of two surface domains. In order to make the multiple domain nature more evident, we prepared lipid-polymer nanoparticles with 50% amine and 50% maleimide, FIGS. 8A-8D. Carboxylated quantum dots labeled amine functional groups on one half the surface while gold nanoparticles labeled the remaining half.

A TEM cross section image of a lipid-polymer hybrid nanoparticle shows a clear distribution of the gold nanoparticles and quantum dots in the regions that were chemically modified with maleimide and amine functional groups, shown in FIGS. 8A-8D. The spatial segregation feature of the nanoparticles is evidently observed in these figures, where quantum dots and gold nanoparticles are located in two different hemispheres. This result indicates that amine functional groups segregated from maleimide functional groups. FIGS. 8A-8D shows several images in which it is possible to observe such segregation in a different spatial arrangement at different magnifications over the surface of the nanoparticle. Sometimes such arrangement is clearly shown in two different hemispheres (FIG. 8A), whereas in other instances, the two functional group segregations seem to appear closer within the same hemisphere (FIG. 8B), indicating the formation of a mosaic pattern. In either of these scenarios, the fact that two different functional groups assembly themselves independently from each (e.g., in clusters) other is advantageous for several types of applications.

FIGS. 7 and 8 clearly show by blending two specific functional groups (i.e., amine-methoxyl and amine-maleimide) one can generate two segregated hemispheres in a wide range of biodegradable nanoparticles including lipid-polymer hybrid nanoparticles, PLGA and PLA. The multiple functionalized surface domains will emerge in each of these cases as long as amine-methoxyl or amine-maleimide mixture is present in a 50% ratio.

Example 3

Characterization of Nanoparticles

Figure 9:
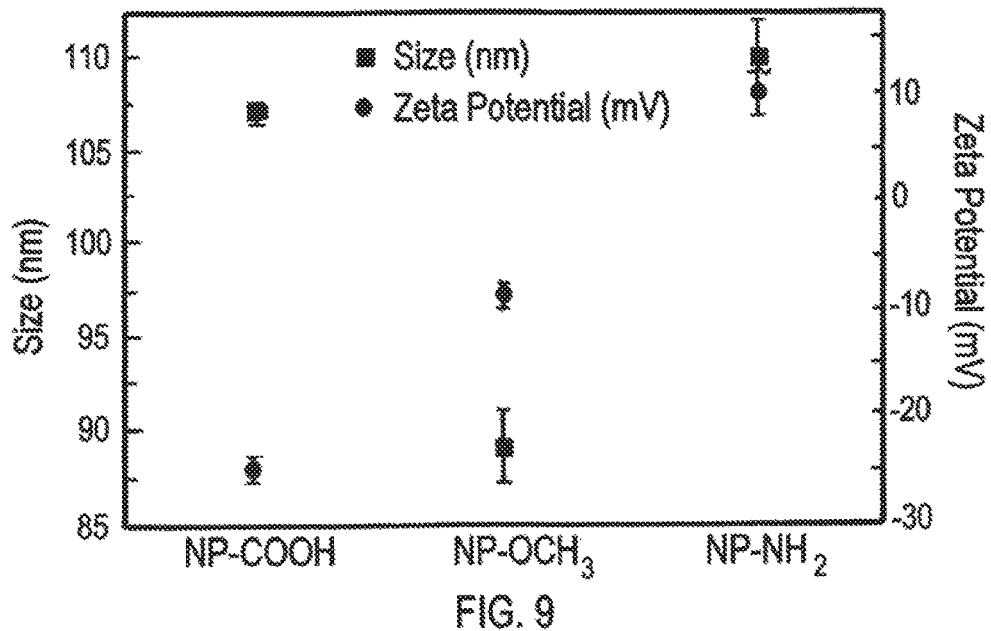
FIG. 9 is a bar graph that shows the size and surface zeta potential of functionalized lipid-polymer hybrid nanoparticles. The nanoparticles are comprised of a poly (D, L-lactide-co-glycolide)(PLGA) core, a polyethylene glycol (PEG) shell, and a lipid monolayer at the interface of the core and the shell. The lipid-PEG molecules serve as the heterofunctional linkers in these particles.

Lipid-polymer hybrid nanoparticles were prepared by functionalizing with amine surface group (NP—$NH_2$) or carboxyl surface group (NP—COOH) or methoxyl surface group (NP—OCH3), FIG. 9. Depending on which surface group was used, the following protocol was followed using the appropriately functionalized polymers.

Poly (D, L-lactide-co-glycolide)-Lipid poly (ethylene glycol) nanoparticles (PLGA-Lipid-PEG particles) were prepared using the following protocol. PLGA polymer was dissolved in acetonitrile at a concentration of 2 mg/mL. The lipid lecithin (Alfa Aesar) was mixed with 1, 2-Distearoyl-sn-Glycero-3-Phosphoethanolamine-N-[Carboxy (Polyethylene Glycol) 2000] (DSPE-PEG-COOH)(Avanti Polar Lipids) at a molar ratio of 8.5:1.5 and dissolved in 4% ethanol aqueous solution. The total lipid weight (lecithin+DSPE-PEG-COOH) was 15% of the PLGA polymer. The lipid solution was preheated at 65° C. for 3 minutes, and the PLGA solution was added dropwise under gentle stirring. The mixed solution was vortexed vigorously for 3 minutes followed by gentle stirring for 2 hours at room temperature. Finally the nanoparticles were washed three times using Amicon® Ultra-4 centrifugal filters (Millipore, Billerica, Mass.) with a molecular weight cutoff of 10K Da.

Size and zeta potential of functionalized lipid-polymer particles are similar between each other. Carboxyl and methloxyl-ends' lipid-polymer particle have negative charge whereas amine-ends' lipid-polymer nanoparticles have positive charge. Therefore, the data clearly shows that the production of functionalized particles with multiple surface domains by following the above protocol have excellent reproducibility.

Example 4

Figure 10A:
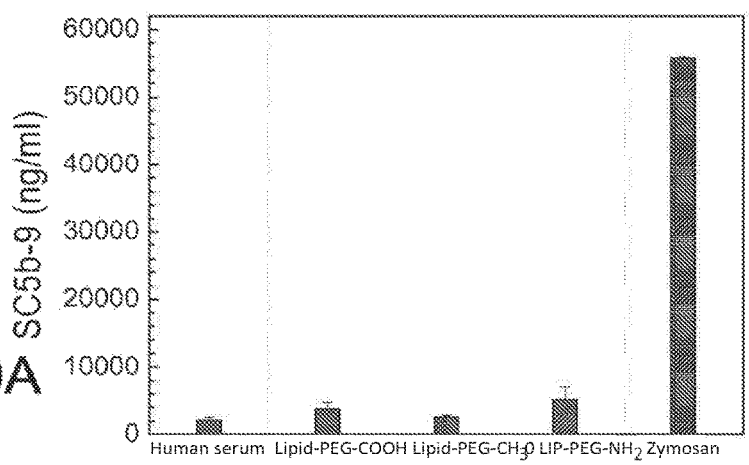
FIGS. 10A, 10B and 10C are bar graphs that show the results of a human serum complement system activation assay using lipid-polymer hybrid nanoparticles surface functionalized with carboxyl, methoxyl, and amine groups.
Figure 10B:
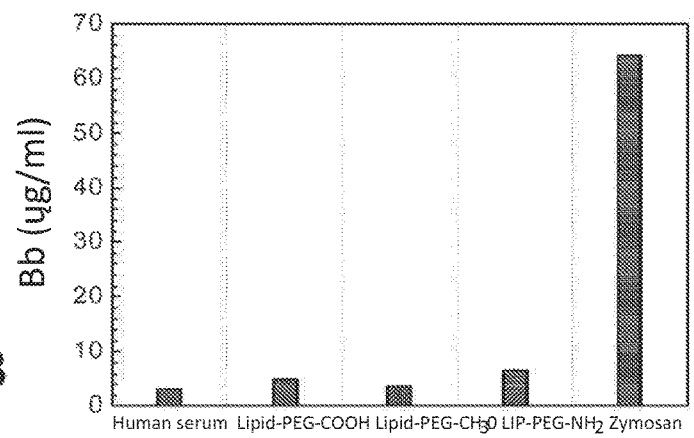
Figure 10C:
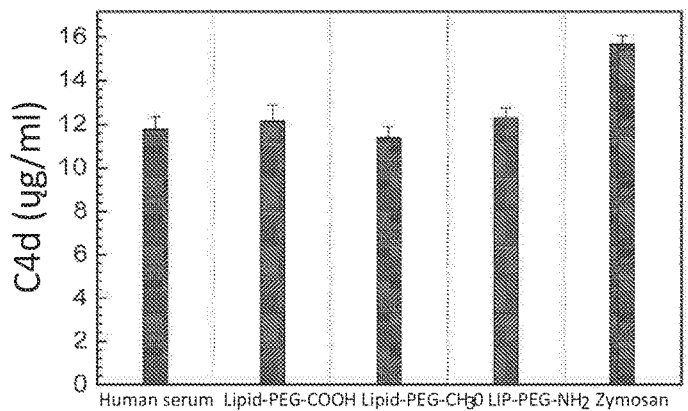

Complement System Activation Studies Using Particles with Mono-Surface Functionalized Domains Lipid polymer hybrid particles were prepared using a modified nanoprecipitation method as described in Example 1. Data from human serum complement system activation assay using lipid-polymer hybrid nanoparticles surface functionalized with carboxyl, methoxyl and amine groups is shown in FIGS. 10A, 10B, and 10C.

All three nanoparticles formulations activate the complement system slightly more than human serum (negative control) but significantly less than Zymosan (positive control), a well-known complement system activator of the alternative pathway. It was also found that lipid-polymer hybrid nanoparticles with amine surface group (—$NH_2$) activate the complement system more effectively than nanoparticles with carboxyl (—COOH) or methoxyl (—$OCH_3$) surface groups. Further studies found that these nanoparticles activate the alternative pathway (FIG. 10B), but not the lectin pathway (data not shown). As compared to human serum without any nanoparticles (negative control), negligible complement system activation via the classical pathway was noted, as NP—COOH and NP—$NH_2$ and NP—$OCH_3$ did not activate the classical pathway (FIG. 10 C).

To assess complement system activation of the lipid-polymer hybrid nanoparticles in vitro, three complement split products, SC5b-9, Bb and 4cd (FIGS. 10A, 10B, and 10C, respectively for each of the three complement split products) were measured using enzyme-linked immunosorbent assay kits from Quidel Corp. (San Diego Calif., USA). SC5b-9 is the S-protein-bound form of the terminal complex, a sensitive biomarker of C5a formation via both the classical and the alternative pathways. Bb is the proteolytically active fragment of factor B, a biomarker of the complement system activation via the alternative pathway. C4d measures the amount of the C4d-containing activation fragments of C4 (C4b, iC4b, and C4d), a biomarker of the complement system activation via the classical pathway. For this study, the nanoparticles were incubated with human serum with a volume ratio of 1:5 in a shaking incubator (80 rpm) at 37° C. for 1 hour.

After incubation the reaction was stopped by adding 20 times volume of PBS solution with contains 0.05 wt % Tween-20, 2.5 wt % protein stabilizers and 0.035 wt % ProClin 300. Then proper kits were used to assay the complement system activation of the nanoparticles following the protocol provided by the kits manufacture. Zymosan was used as a positive control for the alternative pathway and terminal cascade. The complement system activation via the lectin pathway was assessed by the ALPCO Diagnostics kit (Salem, USA). To assess the genuine activation of the complement system via the alternative pathway human scrum was diluted 1:1 in volume with Mg-EGTA buffer.

FIG. 10A is data from complement system activation at the terminal cascade. Bars represent the mean concentration of SC5b-9, a sensitive biomarker of C5a formation via both the alternative pathway and the classical pathway. The results were obtained from three independent experiments with a 95% confidential interval. FIG. 10B is data from complement system activation via the alternative pathway. Bb is the proteolytically active fragment of factor B, a biomarker of the complement system activation via the alternative pathway. FIG. 10C is data from complement system activation via the classical pathway. C4d measures the amount of C4d-containing activation fragments of C4, a biomarker of the complement system activation via the classical pathway. Our results partially agree with complement system literature since C3b bound covalently to the amine groups present on the surface of Lipid-PEG-NH$_2$ nanoparticles. Lipid-PEG-COOH nanoparticles holding a negative charge activated the classical pathway. Also, it can be clearly seen that carboxyl and methoxyl-ends lipid polymer nanoparticles are activators of the human serum alternative pathway.

Example 5

Complement System Activation Studies Using Particles with Multiple Surface Functional Domains The human serum complement system activation induced by the presence of lipid-polymer nanoparticles functionalized with all the possible combination resulting from the mixture of carboxyl, methoxyl and amine groups can be correlated with the charge of these nanoparticles. To determine this, lipid polymer hybrid particles were prepared using a modified nanoprecipitation method as described in Example 2.

Figure 11A:
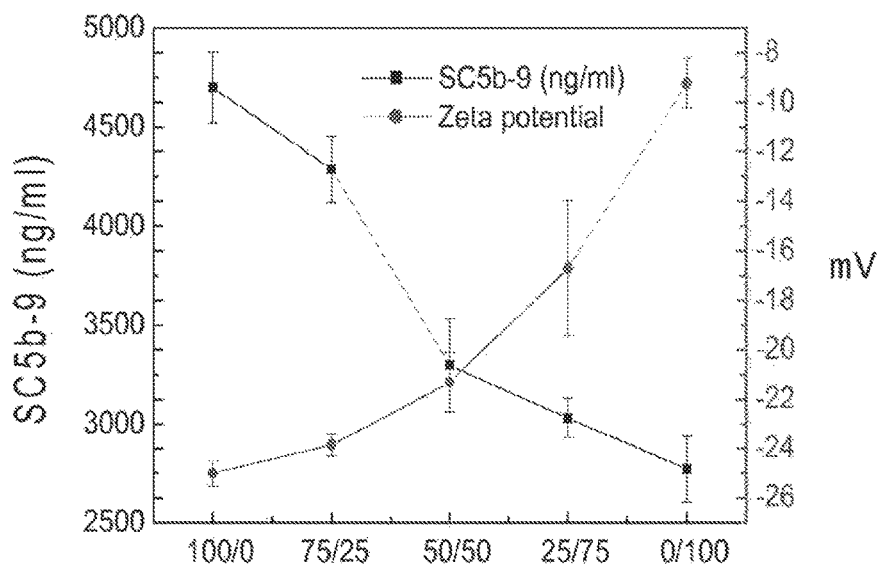
FIGS. 11A and 11B are a graph and a gel, respectively, that show the results of a human serum complement system activation assay and zeta potential using lipid-polymer hybrid nanoparticles as function of carboxyl (nanoparticle-COOH) and methoxyl (nanoparticle-OCH$_3$) surface group compositions.
Figure 11B:
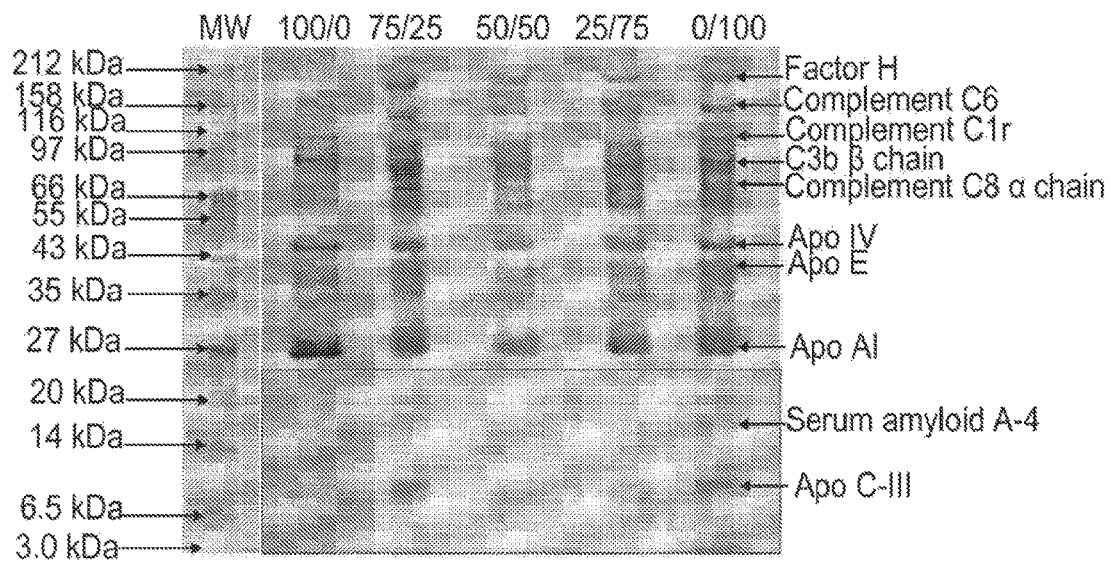

For NPs-COOH/OCH$_3$ (FIG. 11A), increase of methoxyl group on the nanoparticle surface decreases the zeta potential (less negative) while reducing the level of complement activation of the nanoparticles. For example, when the molar ratio of COOH/OCH$_3$ varied from 75/25 to 50/50 and to 25/75, the nanoparticle surface zeta potential was approximately −23 mV, −21 mV and −17 mV respectively. The SC5b-9 concentration decreased from 4287 ng/ml to 3298 ng/ml and 3030 ng/ml). As shown in FIG. 11B, Apo C-III is the human serum protein that bound to NP—COOH/OCH$_3$ at all ratios: 100/0, 75/25, 50/50, 25/75, 0/100. Serum amyloid A4 protein only bound to NP—COOH 100/0 molar ratio.

Figure 12B:
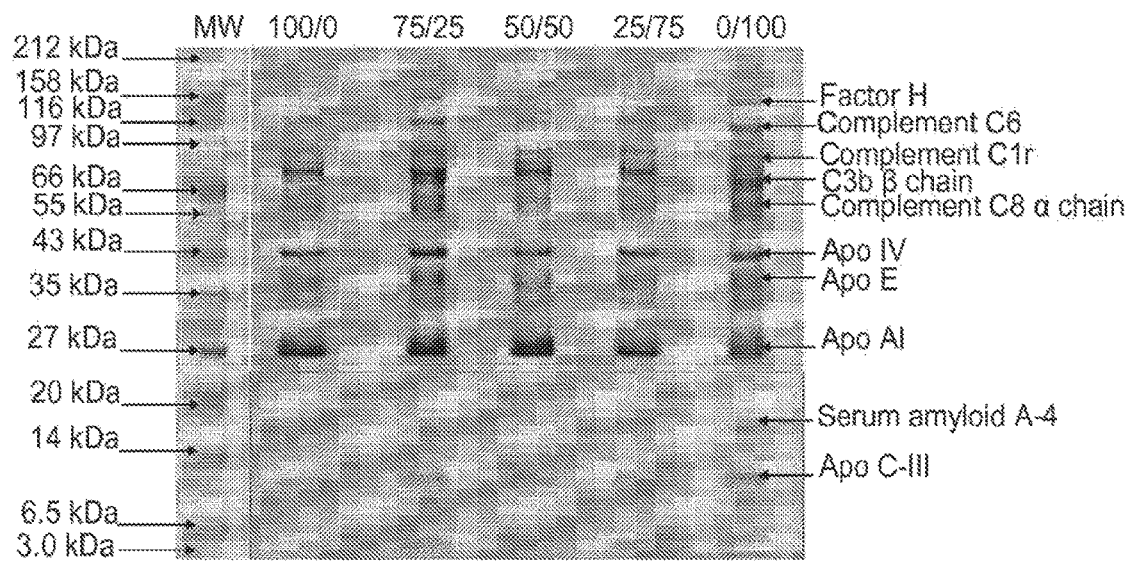

When lipid-polymer nanoparticles are functionalized with a mixture of carboxyl and amine groups (FIG. 12A), a different behavior in charge and complement activation are observed. As the percentage of amino in the mixture increases the more positive is the zeta potential and high levels of complement activation are induced (FIG. 12B). Contrary, in the mixture of amine and methoxyl groups, as the percentage of amine groups diminishes the zeta potential becomes negative and complement activation levels also diminishes (FIGS. 13A and 13B). It is clear that the mixture of carboxyl, methoxyl and amine groups render different physico-chemical characteristic to lipid-polymer nanoparticles. Such surface chemistry modifications have an effect in the levels of complement activation induced by those nanoparticles.

Factor H, the main down-regulator of the alternative pathway was bound less to carboxylic-end lipid polymer nanoparticles than to the methoxyl and amine-ends nanoparticles as shown in FIGS. 11A and 11B, FIGS. 12A and 12B and, FIGS. 13A and 13B and Table 1. Table 1 shows that the less is the amount of factor H bound to carboxylic-ends lipid-polymer nanoparticles the higher is the complement activation. There is no correlation between the levels of complement activation induced by methoxyl, amine-ends lipid nanoparticles and the amount of factor H bound to them.

The amount of factor H (Table 2) and C3b β chain proteins bound to 75/25 Lipid-PEG-COOH/CH$_3$, COOH/NH$_2$ and NH$_2$/CH$_3$ nanoparticles seems to be correlated with the levels of complement activation induced by them. The amount of Factor H or C3b bound to the nanoparticles will determine whether the levels of complement activation are high or low. Factor H bound less to 75/25 Lipid-PEG-COO/CH$_3$ than to 75/25 Lipid-PEG-COOH/NH$_2$ and the same as Lipid-PEG-NH$_2$/CH$_3$ as indicated in Tables 2, 3, and 4. The highest amount of C3bβ chain was observed in Lipid-PEG-NH$_2$/CH$_2$ which rendered the highest complement activation when compared to the one induced by Lipid-PEG-COOH/CH$_3$ and Lipid-PEG-COOH/NH$_2$. Furthermore, according to Table 5, lipid-polymer nanoparticles functionalized with carboxylic groups bound the higher amount of fibrinogen α chain in comparison to amine-end lipid polymer nanoparticles.

TABLE 1

Quantification of Human Serum Proteins Binding to Lipid-Polymer Hybrid Nanoparticles with Different Surface Functional Groups

| Human serum proteins | Amount of protein bound | | |
|---|---|---|---|
| | COOH | CH$_3$O | NH$_2$ |
| Factor H | 0.98 | 1 | 0.94 |
| Complement component C6 precursor | 1.02 | 1 | 0.86 |
| Complement C1r subcomponent precursor | 0.89 | 1 | 0.89 |
| C3b β chain | 0.97 | 1 | 0.98 |
| Complement component C8α chain precursor | 1.02 | 1 | 0.91 |
| Apolipoprotein IV | 0.72 | 1 | 0.87 |
| Apolipoprotein E | 0.80 | 1 | 0.84 |
| Apolipoprotein AI | 1.05 | 1 | 1.06 |
| Serum amyloid A-4 protein precursor | 0 | 1 | 0.92 |
| Apolipoprotein C-III | 1.01 | 1 | 0.95 |

The protein binding density, characteristic of integrated density value (IDV), was obtained by using the software of the FluorCHEM quantitative imaging system (Alpha Innotech). For clarity reason, the IDVs of each protein binding to PLGA-Lipid-PEG-COOH, PLGA-Lipid-PEG-NH$_2$ and PLGA-Lipid-PEG-OCH$_3$ nanoparticles, respectively, were normalized to the IDV of PLGA-Lipid-PEG-OCH$_3$ nanoparticles. Smaller IDV number represents higher amount of protein binding to the nanoparticles

TABLE 2

Quantification of Human Serum Proteins Binding to Lipid-Polymer Hybrid Nanoparticles with a Mixture of Carboxyl and Methoxyl Surface Groups

| Human serum proteins | Amount of protein bound | | |
|---|---|---|---|
| | 75/25 | 50/50 | 25/75 |
| Factor H | 0.73 | 1 | 0.91 |
| Complement component C6 precursor | 0.72 | 1 | 0.85 |
| Complement C1r subcomponent precursor | 0.70 | 1 | 0.80 |
| C3b β chain | 0.80 | 1 | 0.71 |
| Complement component C8α chain precursor | 0.68 | 1 | 0.95 |
| Apolipoprotein IV | 0.85 | 1 | 0.83 |
| Apolipoprotein E | 0.69 | 1 | 0.80 |
| Apolipoprotein AI | 1.20 | 1 | 0.95 |
| Serum amyloid A-4 protein precursor | — | 1 | — |
| Apolipoprotein C-III | 0.77 | 1 | 0.86 |

The numbers of 75/25, 50/50 and 25/75 represent the molar ratios of the carboxyl group to the methoxyl group (COOH/CH$_3$).

TABLE 3

Quantification of Human Serum Proteins Binding
to Lipid-Polymer Hybrid Nanoparticles with a
Mixture of Carboxyl and Amine Surface Groups

| Human serum proteins | Amount of protein bound | | |
|---|---|---|---|
| | 75/25 | 50/50 | 25/75 |
| Factor H | 0.82 | 1 | 1 |
| Complement component C6 precursor | 0.72 | 1 | 0.87 |
| Complement C1r subcomponent precursor | 0.79 | 1 | 1 |
| C3b β chain | 0.58 | 1 | 0.98 |
| Complement component C8α chain precursor | 0.72 | 1 | 1.04 |
| Apolipoprotein IV | 0.66 | 1 | 0.83 |
| Apolipoprotein E | 0.78 | 1 | 1.21 |
| Apolipoprotein AI | 2.08 | 1 | 3.71 |
| Serum amyloid A-4 protein precursor | — | 1 | — |
| Apolipoprotein C-III | 0.85 | 1 | 0.96 |

The numbers of 75/25, 50/50 and 25/75 represent the molar ratios of the carboxyl group to the amine group ($COOH/NH_2$).

TABLE 4

Quantification of Human Serum Proteins Binding
to Lipid-Polymer Hybrid Nanoparticles with a
Mixture of Amine and Methoxyl Surface Groups

| Human serum proteins | Amount of protein bound | | |
|---|---|---|---|
| | 75/25 | 50/50 | 25/75 |
| Factor H | 0.73 | 1 | 0.80 |
| Complement component C6 precursor | 0.53 | 1 | 0.80 |
| Complement C1r subcomponent precursor | 0.92 | 1 | 0.87 |
| C3b β chain | 0.48 | 1 | 0.91 |
| Complement component C8α chain precursor | 0.47 | 1 | 0.76 |
| Apolipoprotein IV | 0.69 | 1 | 1.00 |
| Apolipoprotein E | 0.48 | 1 | 0.93 |
| Apolipoprotein AI | 0.42 | 1 | 0.92 |
| Serum amyloid A-4 protein precursor | 1.16 | 1 | 1.21 |
| Apolipoprotein C-III | 0.59 | 1 | 0.74 |

The numbers of 75/25, 50/50 and 25/75 represent the molar ratios of amine group to the methoxyl group ($NH_2/CH_3$).

TABLE 5

Quantification of Human Plasma Proteins Binding to Lipid-Polymer
Hybrid Nanoparticles with Different Surface Functional Groups

| Human plasma proteins | Amount of protein bound | | |
|---|---|---|---|
| | COOH | $CH_2O$ | $NH_2$ |
| Factor H | 0.51 | 1 | 1.09 |
| Complement component C6 precursor | 1.10 | 1 | 1.17 |
| Complement C1r subcomponent precursor | 1.04 | 1 | 1.07 |
| Fibrinogen α chain | 0.83 | 1 | 1.18 |
| Fibrinogen β chain | 1.18 | 1 | 1.06 |
| Fibrinogen γ chain | 1.16 | 1 | 0.96 |
| Apolipoprotein IV | 1.31 | 1 | 1.27 |
| Apolipoprotein E | 1.22 | 1 | 1.05 |
| Apolipoprotein AI | 0.89 | 1 | 1.32 |
| Serum amyloid A-4 protein precursor | 1.06 | 1 | 1.03 |
| Apolipoprotein C-III | — | 1 | 1.03 |

The table shows the amount of plasma proteins that bound to each functionalized particle.

Example 6

Serum and Protein Binding Study

Gel electrophoresis results of human plasma proteins binding to the lipid-polymer hybrid nanoparticles with a mixture of surface functional groups: carboxyl, methoxyl and amine groups were determined as shown in FIG. 14. To test this lipid polymer hybrid particles were first prepared using a modified nanoprecipitation method as described in Example 2.

As shown in FIG. 14, human serum and human plasma have similar adsorption patterns on the hybrid NPs, except for the binding of fibrinogen. Fibrinogen alpha chain bound less effectively to NP—COOH than to NP—$OCH_3$ and NP—$NH_2$. This figure also shows that human plasma proteins with smaller molecular weight (such as the apolipoprotein family) bound more easily to the hybrid NPs. In addition, FIG. 14 shows that a small amount of factor H and complement proteins C6, C8, and C1r bound to the NP—$NH_2/OCH_3$, but there was little binding of apolipoprotein AI, serum amyloid A4 or apolipoprotein C-III.

Lipid-polymer hybrid nanoparticles were incubated with diluted 1:1 volume human serum or human plasma under gentle shaking of 80 rpm at 37° C. for 1 hour. After incubation the nanoparticles were spun down using a centrifuge at 13000 rpm for 15 minutes and the supernatant was removed. The same procedure was repeated 5 times. Next the nanoparticles were reduced by 25 mM DTT and heated for 10 minutes at 95° C. for 10 minutes. Then the nanoparticle samples were loaded and run through a gradient gel (4-12%) at 150 V for 70 minutes. The gel was stained with Coomassie blue. The bands formed in the gel were analyzed by mass spectrometry (MIT Proteomics core facility).

The human serum and plasma protein adsorption phenomenon observed on different nanomaterials have been studied previously. All these studies mainly report the presence of the family of apolipoproteins (A-IV, E, A-I, C-III), albumin and fibrinogen. However the presence of factor H has only been shown in modified carbon nanotubes studies[15] and in this study. Factor H, the main down regulator of the alternative pathway in plasma consists of 20 short consensus repeat domains (SCRs), each about 60 residues long. The carboxyl-terminal region (SCRs 19-20, FH 19-20) is unique in that it can bind to C3b/C3d. Also, the structure of FH modules 6-8 reveals multiple sulphated sugar-binding sites.

The study of the human serum and plasma proteins bound to functionalized lipid-polymer nanoparticles is also important in that it is a key factor for the nanoparticles' in vivo organ distribution. The results from the data clearly show that part of the fibrinogen, the human plasma, and serum protein patterns look very similar. Furthermore, the human serum and plasma protein binding studies allow the identification of the binding of two key complement proteins: Factor H and C3b β chain. These proteins play a pivotal role in the activation of the complement system via the alternative pathway. Altogether, the results from FIG. 14 clearly show that functional groups on the surface of these nanoparticles can also bind to human plasma proteins with low molecular weight such as the family of apolipoproteins.

Example 7

Coagulation Studies

Coagulation time of human plasma in the absence and presence, respectively, of lipid-polymer hybrid nanoparticles was tested, FIG. 15. The nanoparticle surface is purely covered by methoxyl group (PLGA-Lipid-PEG-OCH$_3$) as described previously. The coagulation assays used for the measurements include Prothrombin (PT), Activated Partial Thromboplastin Time (APTT), and Thrombin Time (TT).

Lipid-polymer hybrid nanoparticles with methoxyl surface group (PLGA-Lipid-PEG-OCH$_3$) were incubated with fresh human citrated plasma under gentle shaking of 80 rpm at 37° C. for 30 minutes. As negative controls, the nanoparticles were incubated with human plasma and 1×PBS buffer in parallel. Triplicate samples were prepared for each condition. After incubation, the samples were measured for Prothrombin (PT), Activated Partial Thromboplastin Time (APTT) and Thrombin Time (TT). These measurements were done by the clinical lab, haematology section, at Brigham and Women's Hospital.

Fibrinogen being one of the most abundant proteins in human plasma required special attention, because it has the potential to activate the coagulation cascade and can play a role in the opsonization process execute by the complement system. Since Lipid-PEG-CH$_3$ nanoparticles induced the lowest complement activation, they were chosen to conduct further immunocompatibility studies. Coagulation assays including Prothrombin time (PT), Activated partial thromboplastin time (APTT), and thrombin time were conducted with these nanoparticles. PT is the time that it takes plasma to clot. It is a measurement of the function of the extrinsic pathway. This test measures the presence of factors II, V, VII, X and fibrinogen. The reference range for prothrombin time is usually around 12-15 seconds. APTT measures the performance of the intrinsic and common coagulations pathways. Thrombin converts fibrinogen to an active form that assembles into fibrin and assures the good performance of the coagulation cascade.

The results show that the presence of methoxyl-end lipid polymer nanoparticles have no effect on the clotting time in plasma since no variation in clotting time was observed when plasma was incubated with or without Lipid-PEG-CH$_3$O. An insignificant change in the APTT was induced by the presence of Lipid-PEG-CH$_3$O (FIG. 15). Any change in the thrombin time was generated when human plasma was incubated with Lipid-PEG-CH$_3$. In general these coagulation assays suggest that these nanoparticles do not have any effect on the coagulation system.

Example 8

Particles with Multiple Functionalized Surface Domains for Prostate Cancer Treatment The new particles can be used to help treat prostate cancer by targeting therapeutic drugs to the cancerous tissue or cells. Lipid polymer hybrid particles are prepared using a modified nanoprecipitation method as described in Example 2. One of the surface targeting moieties specific for prostate cancer treatment is the A10 RNA aptamer. A second functional group is a methoxyl group to minimize complement system activation before and after particle binding. Carboxyl terminated lipid-PEG is first activated to NHS ester using 1-ethyl-3-(3-dimethylaminopropyl)carbodiimide (EDC) and N-hydroxysuccinimide (NHS) activation chemistry in ultra pure water. After activation, amine terminated A10 RNA aptamers are added into lipid-PEG solution. The lipid-PEG-aptamer conjugates are used in the self-assembly of lipid-polymer hybrid particles.

The A10 aptamer is a nuclease-stabilized 2'-fluoropyrimidine RNA molecule with 57 base pairs which has shown high binding affinity to the prostate specific membrane antigen (PSMA) overexpressed by some prostate cancer (PCa) cell lines. LNCaP prostate adenocarcinomas, which express the PSMA antigen on their plasma membrane, are chosen as the prostate cancer model cell line for in vitro testing; PC3 prostate adenocarcinomas, which do not express the PSMA antigen, were employed as a negative control.

Example 9

Preparation of Nanoparticles/Microparticles with Multiple Different Functional Groups Lipid-polymer hybrid nanoparticles were prepared by functionalizing half of PLGA-Lecithin-PEG nanoparticles with 50% NH$_2$ and 50% maleimide surface as described in Example 2.

Lipid-polymer hybrid microparticles were prepared by functionalizing half of PLGA with 50% DSPE-PEG-NH$_2$ and 50% DSPE-PEG-MAL using the emulsion method. Briefly, PLGA was dissolved in ethyl acetate. The functional groups were suspended in 4% ethanol and mixed them. This mixture was exposed to a homogenizer tip for 15 seconds at 1000 rpm. Immediately, the PLGA was added dropwise and the homogenizer tip was located at the interface of ethanol and ethyl acetate. The mixture was sonicated for 1 minute at 8000 rpm. Fifty ml of H$_2$O was added to each sample. Samples were stirred overnight. Remaining solvent was filtered with 100 kda amicon filters. Subsequently, PLGA-PEG-NH$_2$ was suspended in PBS and reacted with gold nanoparticles for 1 hour at 4° C. Particles were washed three times with MQ water followed by filtration. Polymeric particles samples were examined with transmission electron microscope and scanning electron microscope. TEM images were obtained using a 1200 (JEOL, JAPAN) with an accelerating voltage of 80 kV.

Nanoparticles were loaded on a copper grid and stained with uranyl acetate. SEM was performed using a FEI XL30 FEG-ESEM. The images are back-scattered electron images taken with low vacuum. The acceleration voltage was chosen between 3-8 kv.

Furthermore, for protein analysis nanoparticles or microparticles functionalized with 50% NH2 and 50% Mal were suspended in 1 ml of MQ water and 500 micrograms of Sulfo-LC-SPDP was added to the vial. The excess of sulfo-LC-SPDP was removed by filtration. Samples were incubated for 30 minutes followed by three washes with water using 100 kDa Amicon® filter. Nanoparticles or microparticles were resuspended in PBS and 10 μg of unlabelled or labelled C3d was added to the mixture and left the samples to incubate for 4 hours at 4° C. After the incubation time nanoparticles or microparticles were washed and pelleted. The supernatant was discarded and 20 μl of sample buffer (0.2 M Tris, 8M urea, 2% SDS, 0.2 M EDTA, 40 mM dithiothreitol (DTT), adjusted to pH 8.2 with HCl) was added to samples. Samples were heated at 100° C. for 10 minutes and run in at SDS-PAGE as described below.

The samples that required electrophoretic analysis were incubated at 95° C. for 5 minutes in samples buffer (as described above) and loaded on a 4-12% Novex® Bis-Tris sodium dodecyl sulphate-polyacrylamide gel electrophoresis (SDS-PAGE) gradient gel (Invitrogen, Paisley, UK), then separated by electrophoresis for 50 minutes at 150 V using MES buffer (Invitrogen) in a Novex X Cell II Mini-cell gel apparatus. Proteins bands were stained with Simply Blue Safe Stain (Invitrogen). Protein transfer from SDS-PAGE gels to a cellulose transfer membrane was carried out using a wet western blot system. The gel and the membrane were soaked in transfer buffer (TBST) (4.84 g Tris, 58.48 g NaCl, 1.0 ml Tween® 20, pH 7.4) before application of a constant current at 0.4 A for 180 minutes. The membrane was then blocked in TBST containing 4% BSA in TBST for 1 hour at RT. The membrane was incubated with polyclonal Anti-C3d (rabbit) diluted 1:100 in TBST buffer for 1 hour at RT with gently shaking After three washes with TBST for 5 minutes, the membrane was incubated with 10 ml of TBST containing anti-rabbit HRP (1:4000) for 30 minutes, and 1 hour at RT. The membrane was washed six times as before and the proteins were detected by Pierce West Pico.

The formation of particles with multiple functionalized surface domains was also observed at the micro-scale with polymeric nanoparticles as shown by TEM (FIG. 16A), scanning electron microscopy (SEM) (FIG. 16B), and energy disperse X-ray (EDX) (FIG. 16C). Phase-segregation of polymer nanoparticles is clearly observed by TEM, where half of the microparticles was functionalized with 50% MAL and 50% $NH_2$ and traced it with gold nanoparticles (FIG. 16A). The black region of the nanoparticles indicates the presence of gold. These microparticles were also characterized by SEM and coated with carbon to enhance the contrast (FIG. 16B). An EDX spectrum was taken from these samples to corroborate the presence of gold nanoparticles on the surface of microparticles (FIG. 16C).

To explore the possibility of using them as a novel vaccine platform we attached one side of the particles with an adjuvant molecule and on the other side an antigen. This antigen can be virus, fungus, etc. We chose C3d as the antigen, because it is a complement protein that can serves as strong natural adjuvant. Turkey egg lysozyme (TEL) was chosen as the antigen. Having C3d and TEL on the same nanoparticles, but located in a different regional space on the surface of the nanoparticle, would induce a strong immune response. Western blot studies showed the presence of the C3d on nanoparticles or microparticles that were bound to particles as shown in FIGS. 17A and 17B respectively. The thiol bond created between the SH groups of C3d and the amine functional groups of the particles was broken by the reducing agents DTT and the denature conditions of the gel. Clearly FIGS. 17A and 17B show that a potential adjuvant molecule and an antigen can be placed on two different hemispheres of microparticles.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method of delivering an agent to a subject, the method comprising
   (i) obtaining a composition comprising a plurality of particles having multiple functionalized surface domains, the particles comprising
      (a) a core structure having a surface; a plurality of first linkers, each comprising a first end that binds to the surface of the core structure, and a second end that comprises a first functional group; and a plurality of second linkers, each comprising a first end that binds to the surface of the core structure, and a second end that comprises a second functional group, wherein the first and second functional groups are different; wherein the linkers are bound to the surface of the core structure via their respective first ends, and wherein the first and second functional groups form an external mosaic of surface domains, a majority of each domain comprising one type of functional group, and
      (b) therapeutic, prophylactic, or diagnostic agents; and
   (ii) administering to the subject the composition.

2. The method of claim 1 for imaging a region of a subject, the method comprising
   administering the composition wherein the agent is a diagnostic agent; and detecting the the diagnostic agent.

3. The method of claim 1 for treating a disorder in a subject in need thereof, the method comprising administering to the subject the composition wherein the agent is a therapeutic or prophylactic agent selected to treat the disorder.

* * * * *